US011523759B1

(12) United States Patent
Venezky et al.

(10) Patent No.: US 11,523,759 B1
(45) Date of Patent: Dec. 13, 2022

(54) SYSTEM AND METHOD FOR BIOMETRIC MONITORING AND EDUCATIONAL ANALYSIS OPTIMIZATION USING ARTIFICIAL INTELLIGENCE

(71) Applicant: Biometric Edge Inc., New York, NY (US)

(72) Inventors: Elie Venezky, Brooklyn, NY (US); Jimmy Claude Brake, Jr., Mountain View, CA (US)

(73) Assignee: Biometric Edge Inc., New York, NY (US)

( * ) Notice: Subject to any disclaimer, the term of this patent is extended or adjusted under 35 U.S.C. 154(b) by 0 days.

(21) Appl. No.: 17/652,890

(22) Filed: Feb. 28, 2022

(51) Int. Cl.
*A61B 5/16* (2006.01)
*G06F 3/01* (2006.01)
*G06V 40/19* (2022.01)

(52) U.S. Cl.
CPC .............. *A61B 5/163* (2017.08); *A61B 5/165* (2013.01); *G06F 3/013* (2013.01); *G06V 40/19* (2022.01)

(58) Field of Classification Search
CPC .... G06Q 10/10; G06Q 30/02; G06Q 30/0601; G06Q 30/0201; G06Q 50/01; G06Q 20/047; G06Q 20/0655; G06Q 20/3224; G06Q 20/3276; G06Q 50/10; G06Q 50/184; G06Q 10/047; G06Q 10/06; G06Q 10/0637; G06Q 30/0203; G06Q 30/0242; G06Q 30/0282; G06Q 30/0643; G06Q 50/163; G06Q 50/18; G06Q 50/265; G06Q 10/00; G06Q 10/063112; G06Q 10/063116; G06Q 10/0639; G06Q 10/06398; G06Q 10/103; G06Q 10/1091; G06Q 10/1097; G06Q 10/20; G06Q 20/10; G06Q 20/12; G06Q 20/1235; G06Q 20/145; G06Q 20/29; G06Q 20/322; G06Q 20/384; G06Q 20/386; G06Q 30/0243; G06Q 30/0249; G06Q 30/0251; G06Q 30/0255; G06Q 30/0269; G06Q 30/0276; G06Q 30/0613; G06Q 30/0623; G06Q 50/00; G06Q 50/20; G06Q 50/205; G06Q 50/22; G06Q 50/26; A61B 5/16; A61B 5/0002; A61B 5/163; A61B 5/0022; A61B 5/11; A61B 5/14532; A61B 5/4839; A61B 5/7275; A61B 5/7475; A61B 2505/07; A61B 2560/0295; A61B 2560/0475; A61B 3/113; A61B 3/145; A61B 5/00; A61B 5/002; A61B 5/02405; A61B 5/0533; A61B 5/08; A61B 5/1118;
(Continued)

(56) References Cited

U.S. PATENT DOCUMENTS 8,885,882 B1 * 11/2014 Yin .................. G06V 40/19
382/103

* cited by examiner

*Primary Examiner* — Brandi N Thomas
(74) *Attorney, Agent, or Firm* — Kwan & Olynick LLP

(57) ABSTRACT

Systems and methods for educational analysis optimization. The system includes a camera, a processor and memory. The memory stores instructions to execute a method. The method begins with receiving a request from a user at a client device to begin a stimulus session. Then, video recording of the user for the stimulus session is initialized. Next, calibrations for emotions and gaze are set. Then, one or more stimuli are presented to the user. Cues and reactions are recorded and mapped to content that was displayed during the times of recorded reactions and cues. The recordings are post-processed for educational analysis and feedback is provided to the user. The feedback and analysis can be optimized using a predictive artificial intelligence model.

20 Claims, 20 Drawing Sheets

(58) Field of Classification Search
CPC ....... A61B 5/225; A61B 5/369; A61B 5/4064;
A61B 5/4812; A61B 5/4848; A61B
5/4857; A61B 5/486; A61B 5/4866; A61B
5/6897; A61B 5/7225; A61B 5/7278;
A61B 5/7282; A61B 5/743; A61B
1/00057; A61B 3/0058; A61B 3/024;
A61B 3/10; A61B 3/1015; A61B 3/103;
A61B 3/1035; A61B 3/14; A61B 3/152;
A61B 5/055; A61B 5/742; A61B
1/00006; A61B 1/00009; A61B 1/000096;
A61B 1/00016; A61B 1/00163; A61B
1/00172; A61B 1/00193; A61B 1/00194;
A61B 1/0605; A61B 1/0638; A61B
1/0676; A61B 1/31; A61B 2034/2048;
A61B 2560/0223; A61B 2562/0257;
A61B 3/0041; A61B 5/1103; A61B
5/1127; A61B 5/162; A61B 5/165; A61B
5/168; A61B 5/316; A61B 5/4088; A61B
5/4803; A61B 90/39; A61B 18/1485;
A61B 2017/00057; A61B 2018/0016;
A61B 2018/0022; A61B 2018/00226;
A61B 2018/00267; A61B 2018/00517;
A61B 2018/00791; A61B 2018/00839;
A61B 2018/1465; A61B 2018/1475;
A61B 2090/065; A61B 2503/06; A61B
2576/026; A61B 3/0025; A61B 3/0083;
A61B 3/112; A61B 3/12; A61B 5/0004;
A61B 5/0036; A61B 5/0042; A61B
5/0082; A61B 5/015; A61B 5/0538; A61B
5/1121; A61B 5/1122; A61B 5/1128;
A61B 5/1451; A61B 5/1459; A61B
5/167; A61B 5/202; A61B 5/205; A61B
5/24; A61B 5/389; A61B 5/391; A61B
5/4017; A61B 5/4528; A61B 5/4542;
A61B 5/4836; A61B 5/4863; A61B
5/4875; A61B 5/6803; A61B 5/6814;
A61B 5/6848; A61B 5/7246; A61B
5/7257; A61B 5/7267; A61B 5/7405;
A61B 5/7455; A61B 5/746; A61B
6/4233; A61B 6/4417; A61B 6/487; A61B
6/502; G01C 21/32; G01C 21/3815;
G01C 21/3841; G01C 21/3492; G01C
21/3602; G01C 21/3889; G01C 11/02;
G01C 21/206; G01C 21/36; G01C
21/362; G01C 21/3691; G01C 21/3859;
G01C 11/00; G01C 11/06; G01C 15/00;
G01C 21/00; G01C 21/20; G01C 21/24;
G01C 21/26; G01C 21/34; G01C
21/3476; G01C 21/3647; G01C 21/3658;
G01C 21/3667; G01C 21/3804; G01C
21/3807; G01C 21/3819; G01C 21/3837;
G01C 21/3848; G01C 21/3867; G01C
21/3881; G01C 21/3885
See application file for complete search history.

SAT Test

The woman _____ her friends for claiming to care about social justice but refusing to vote in the last election.

- harangued
- cajoled
- disabused
- extolled ated analysis optimization. The system includes a camera, a processor and memory. The memory stores instructions to execute a method. The method begins with receiving a request from a user at a client device to begin a stimulus session. Then, video recording of the user for the stimulus session is initialized. Next, calibrations for emotions and gaze are set. Then, one or more stimuli are presented to the user. Cues and reactions are recorded and mapped to content that was displayed during the times of recorded reactions and cues. The recordings are post-processed for educational analysis and feedback is provided to the user.

SYSTEM AND METHOD FOR BIOMETRIC MONITORING AND EDUCATIONAL ANALYSIS OPTIMIZATION USING ARTIFICIAL INTELLIGENCE

CROSS-REFERENCE TO RELATED APPLICATIONS

This application claims the benefit of prior application U.S. Provisional Application No. 63/131,735, filed Dec. 29, 2020, titled "SYSTEM AND METHOD FOR BIOMETRIC MONITORING AND EDUCATIONAL ANALYSIS OPTIMIZATION USING ARTIFICIAL INTELLIGENCE" by Elie Venezky et al., which is herein incorporated by reference in its entirety for all purposes.

TECHNICAL FIELD

The present disclosure relates to the field of biometrics, and specifically to biometric analysis for educational analysis.

BACKGROUND

Education is an important part of life. For most people, education consists of going to school and taking tests. However, taking tests is not easy for everyone. Even if a student knows a lot about a subject, the student might not be a great test taker. There are many reasons why many people struggle with taking tests. One reason might be concentration or pressure. Another reason may be that the student does not have the best strategy for taking tests. Even though tests may not be the most accurate method to determine knowledge and understanding, tests still remain one of the most widely accepted vehicles for determining academic performance.

Given the ubiquitous nature of tests, it would be beneficial to learn why certain students are not good test takers. Unfortunately, many factors directly involved in performance during tests cannot easily be determined by humans. In addition, there are many biometric cues corresponding to these factors that cannot be seen by the human eye even when a human is looking directly at the factors. For example, it is very difficult for a human to constantly monitor the human eye reading text. In addition, the human eye cannot get a person's pulse simply by watching them. Further, the human eye cannot measure the movement and dilation of the pupil and iris. These obstacles often cause people to miss important conclusions about education, performance, response to stimuli, and even health care. Thus, there is a need for a system and method for monitoring biometric data to help better understand people and education.

SUMMARY

The following presents a simplified summary of the disclosure in order to provide a basic understanding of certain embodiments of the present disclosure. This summary is not an extensive overview of the disclosure and it does not identify key/critical elements of the present disclosure or delineate the scope of the present disclosure. Its sole purpose is to present some concepts disclosed herein in a simplified form as a prelude to the more detailed description that is presented later.

Aspects of the present disclosure relate to systems, methods, and non-transitory computer readable media for edu- In some embodiments, the stimulus session is a test taking session. In some embodiments, the cues and reactions include one or more of the following: pulse, eye blink rate, eye movement, and pupil dilation. In some embodiments, the stimulus session includes test questions, each test question being tagged with a difficulty level. In some embodiments, post-processing the recorded cues and reactions includes calculating pacing throughout the stimulus session. In some embodiments, includes presenting a graphical representation of the user's performance during the stimulus session. In some embodiments, the method further comprises optimizing the feedback provided using a predictive artificial intelligence (AI) model.

Additional advantages and novel features of these aspects will be set forth in part in the description that follows, and in part will become more apparent to those skilled in the art upon examination of the following or upon learning by practice of the disclosure.

BRIEF DESCRIPTION OF THE DRAWINGS

The disclosure may best be understood by reference to the following description taken in conjunction with the accompanying drawings, which illustrate particular embodiments of the present disclosure. In the description that follows, like parts are marked throughout the specification and drawings with the same numerals, respectively. The drawing figures are not necessarily drawn to scale and certain figures may be shown in exaggerated or generalized form in the interest of clarity and conciseness.

DETAILED DESCRIPTION

Figure 1:
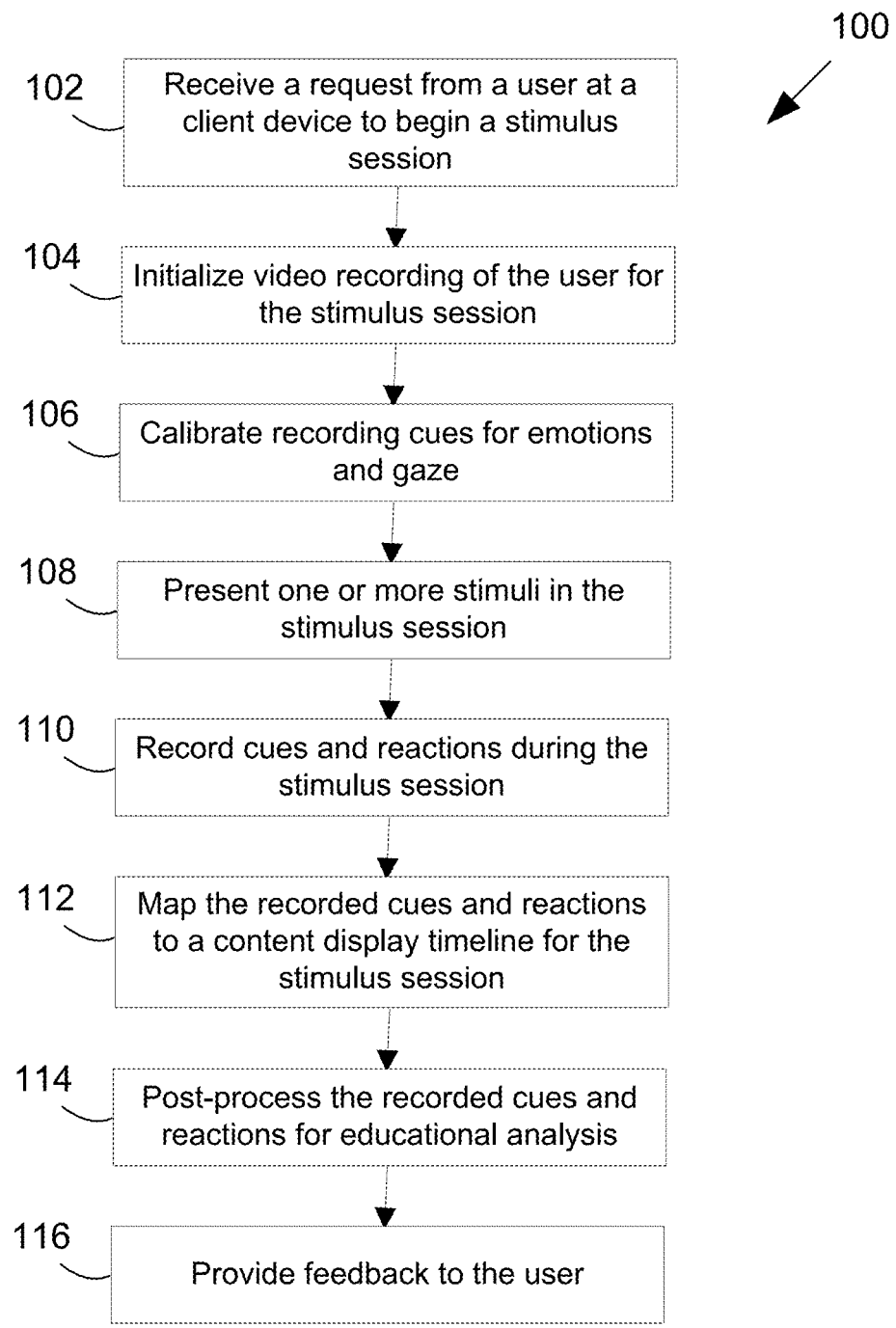
FIG. 1 shows a flow chart of one method for educational analysis optimization, in accordance with embodiments of the present disclosure.

Reference will now be made in detail to some specific examples of the disclosure including the best modes contemplated by the inventors for carrying out the disclosure. Examples of these specific embodiments are illustrated in the accompanying drawings. While the disclosure is described in conjunction with these specific embodiments, it will be understood that it is not intended to limit the disclosure to the described embodiments. On the contrary, it is intended to cover alternatives, modifications, and equivalents as may be included within the spirit and scope of the disclosure as defined by the appended claims.

For example, the techniques of the present disclosure will be described in the context of biometric monitoring and education analysis optimization. However, it should be noted that the techniques of the present disclosure apply to a wide variety of network transactions, collaborative environments, data structures, and different types of data. In the following description, numerous specific details are set forth in order to provide a thorough understanding of the present disclosure. Particular example embodiments of the present disclosure may be implemented without some or all of these specific details. In other instances, well known process operations have not been described in detail in order not to unnecessarily obscure the present disclosure.

Various techniques and mechanisms of the present disclosure will sometimes be described in singular form for clarity. However, it should be noted that some embodiments include multiple iterations of a technique or multiple instantiations of a mechanism unless noted otherwise. For example, a system uses a processor in a variety of contexts. However, it will be appreciated that a system can use multiple processors while remaining within the scope of the present disclosure unless otherwise noted. Furthermore, the techniques and mechanisms of the present disclosure will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

For years, teachers/tutors have been trying to educate kids on how to take tests, but do not actually know what the kids are doing during the actual test. Two factors used in doing well on exams is 1) knowing the material, and 2) knowing how to take an exam. Knowing the material is self-explanatory, but knowing how to take a test involves pacing oneself so that there is enough time to finish the section, not spending too much time on any one question, handling anxiety so it does not affect the score, rereading reading passages when answering questions, and checking one's work.

Knowing the material and knowing how to take a test are intertwined, and often, problems with taking a test are misinterpreted as problems with the material. For example, a student could struggle on reading comprehension because they are reading too fast, or they are not rereading the passage when answering questions. Likewise, a student could be pacing themselves incorrectly and spending too much time on hard questions, forcing them to guess of the questions at the end of the section without reading them.

A regular mock exam just shows a score and which questions a student got wrong, which leads to wrong conclusions: a parent sees that their child missed two probability questions at the end of a section, so they assume that their child struggles with probability. But the student may have guessed on those questions without reading them, and the problem was actually a ratio question halfway through the section that the student got right, but which took them six minutes.

A teacher can instruct a student on the correct way to take a test, but that does not mean that the student is able to do so. Most often, the student may only be doing one or two things wrong but that one mistake leads to a cascade of other issues that causes the student to perform poorly overall.

Thus, there is a need for a way to ensure that students are pacing themselves correctly by measuring how much time they spend on each question and how much time they spend on each reading passage. Teachers can then compare this to the average time students spend on that question or that passage. In addition, there is a need to ensure that students are rereading reading passages when answering questions by tracking their eye movements, and to see if students are checking their work by tracking whether they return to questions. There is also a need to monitor students' pulses to see if they are struggling with anxiety, and cross-reference this information with their performance to see how that anxiety affects their performance.

As mentioned above, there are many biometric cues corresponding to factors that affect test performance. Scientists and researchers have been using biometric data gathered through machines for various purposes, but none have been able to extract the proper biometric data to optimize educational and behavioral analysis. The techniques and mechanisms of the present disclosure, utilize a combination of software and hardware to monitor a student's face, using a camera, and to analyze the student's facial responses to the test. As the student is taking the test, the system monitors their face and the software has the ability to link up what a smile, frown, scrunched eyebrows, pupil dilation, pulse, stress level, and/or emotional reaction, to the questions the student is being asked to answer. That allows the teacher or tutor to get a much better assessment. For example, the system can detect when a pulse rate has spiked, or if student was not even looking at the screen during a specific time period.

Accordingly, techniques and mechanisms of the present disclosure provide for systems and tools that monitor, collect, and store specific physical responses and behaviors by a person, usually a student, while the student performs an online computerized test, and generates results in the form of time graphs showing the student's responses and behaviors throughout the test. Combining physical response and behavior data with the test score will give a teacher or a tutor better insight into a student's experience in taking a test, and therefore may aid in more helpful and productive coaching for the student.

According to various embodiments, the physical responses and behaviors collected and then stored include pulse, eye blink rate, eye movement, and pupil dilation, which are all measured via the computer's camera that is directed at the student's face for the duration of the test. These physical responses give insight into the stress level and emotions the student experiences with each question and throughout the test. For example, if the student faces a particularly tough question, the student's pulse may spike, indicating a higher stress level. In some embodiments, the system will monitor that pulse rate, and through eye tracking, will show exactly where on the test the student is looking while the student experiences the increased pulse.

According to various embodiments, the system also builds specific components into the test itself that aid in the monitoring of the physical response and behavior data. In such embodiments, the graphical user interface is modified to administer tests in a manner such that each question of the test is on its own page, which allows for tracking of page turns, measuring time spent on each question, and seeing if the student re-reads or goes back to a particular question. This provides information on pacing and shows whether there are particular topics or questions that the student finds more challenging than others. Having this information can help teachers and tutors pinpoint a student's specific needs so that they know where to direct more focus while coaching.

In some embodiments, the difficulty level of each individual question is indicated by the test creator. This will help later when a teacher interprets test score results in combination with physical response and behavior data, and can see how much time a student spent on difficult versus easy questions, and if, for instance, the student struggled to complete a test while spending the majority of the allotted time trying to tackle a few tough questions.

In some embodiments, the system has two distinct user roles: a test giver and a test taker. Each user has a customized interface based on the user's role. The test givers will be shown their student profiles and be able to choose tests to assign to each of them through the user interface. In some embodiments, there are also test creator pages that are used in putting together the test. The test takers will be shown the available test for them to perform. According to various embodiments, the test takers will be asked for permission for the system to have access to the computer's camera, and upon being granted that access, the system will be able to monitor the student's face throughout the time the student spends on the test in the software.

In some embodiments, after completion of the test, a teacher or a tutor will be able to see comprehensive results of the student's performance on the test in reports generated by the software. In some embodiments, the results are transformed into a time-based graph on a second by second basis. Such a graph would display biometric factors such as pulse, breathing rate, and pupil dilation to each question and determine, using a predetermined algorithm, the emotional reaction to each question. The teacher will be able to see, for each test question, the length of time the student spent looking at it, whether the student skipped it and went back to it later, the student's stress level as indicated by pulse rate and eye movements, and whether the student's ultimate answer to the question was correct or not. In some embodiments, the results are presented on a special page in a graphical user interface. Having access to this level of information can allow a teacher or tutor to get a much better assessment of a student and help lead to more successful outcomes in educating students on how to take tests.

In some embodiments, they system is also configured to monitor a teacher's reaction to the data generated from the test taking session of a student. In addition, in some embodiments, the system can also be configured to monitor the interactions between the teacher and the student, as well as the student's reaction to the results and the post-test interactions with the teacher. Last, the system can also be configured to monitor whether the student improves during subsequent testing sessions.

According to various embodiments, the method and systems disclosed use cameras and screens that are attached to, or are a part of, a computerized device to capture video of a person while the person watches and interacts with a screen. During the video, the person could be solving problems on the screen, reading, or even speaking. In some embodiments, the video generated by the camera is analyzed in real-time and post-processed to extract detailed biometric and gaze data from the video. In addition, the system can also match extracted data to what was on the screen. In other words, the extracted data is synchronized to data that was displayed on the screen at the time of capture. In some embodiments, the information from the analysis is then used by professionals and or artificial intelligence (AI) to create a report and or action items. In some embodiments, the action items can be providing changes to what the person/subject was viewing or doing on the screen and/or providing feedback to the person about what the person was doing while viewing the screen. For example, if a student took a reading test, but didn't go back to reread the passage when answering questions, an action item might encourage the student to reread the passage when answering questions.

FIG. 1 illustrates a one method for education analysis. Method 100 begins with step 102, receiving a request from a user at a client device to begin a stimulus session. In some embodiments, a stimulus session is an exam or a mock exam of any test or standardized test, such as SAT, ACT, ISEE, SSAT, and SHSAT. At step 104, video recording of the user is initialized for the stimulus session. In some embodiments, this is usually accomplished via a camera or a webcam. At step 106, recording cues are calibrated for emotions and gaze. At step 108, one or more stimuli is presented in the stimulus session. In some embodiments, stimuli can be passages, questions, or instructions. At step 110, cues and reactions are recorded during the stimulus session. In some embodiments, this includes eye movement, facial expressions, and sounds made by the user. At step 112, the recorded cues and reactions are mapped to a content display timeline for the stimulus session. At step 114, the recorded cues and reactions are post-processed for educational analysis. In some embodiments, this includes using pre-determined algorithms and/or AI to determine emotional states and frames of mind during the exam. Last, at step 116, feedback is provided to the user. In some embodiments, the feedback can include, but not limited to, information regarding a user's pulse, blink rate, how long the user spent on every question, how long the average student spends on every question, whether the user went back to check a question, whether the user reread a reading passage when answering related questions, how the user did on the toughest questions, and whether the user is ready for the exam.

In some embodiments, feedback comprises test results as well as a summary of the student's performance during the exam. In some embodiments, the summary includes information such as how the user did on each topic (ratio, algebra, sentence completions, analogies, main point, etc.), how the user did on each level of difficulty (questions are ranked 1-5 for difficulty level), the user's best and worst subject, and how the user did on each subject (general—math, reading, grammar).

In some embodiments, the summary also includes five metrics for "test readiness": test grit, vertical fluidity, test equanimity, time awareness, and overall test readiness, all of which are then displayed as separate sections in the graphical user interface (GUI).

In some embodiments, a "test grit" value is calculated and displayed in the GUI. In some embodiments, certain questions are designated as test grit if they are of a difficulty level of 4 or above (on a 1-5 scale) AND take more than two steps to complete (math), or involve reading a whole passage (reading), or reading contiguous sentences (grammar). In some embodiments, grit is scored as a percent: (number of correct answers on grit questions)÷(total questions marked grit). For example, if out of 10 grit questions, a student answered 6 correctly, then their grit score is: 6/10=60%. As sometime used herein, the terms "value" and "score" may be used interchangeably.

In some embodiments, a "vertical fluidity" value is also calculated and displayed in the GUI. In some embodiments, vertical fluidity measures a student's willingness to reread passages on reading comprehension questions. The system does this in two ways. One, on some tests, the passage is on an earlier screen than the questions, and the system measures automatically whether a student goes back to that previous screen while doing the questions. Two, on some tests, the passage and the question are on the same screen, but the passage is on the left side and the question is on the right. In some embodiments, the system tracks eye movement through the computer's camera to tell if a student is looking at the passage on the left after reading the question on the right. In some embodiments, when this happens, the screen is split in the following way: 40% of the screen is considered the left and contains the passage; 20% of the screen is considered the center and left blank; and 40% of the screen is considered the right and contains the question. In some embodiments, when a student first logs on to take a test, they system first calibrates their eye movement through machine learning techniques. In some embodiments, vertical fluidity is also scored as a percent (Number of reading questions on which they reread the passage)÷(total reading questions)× 100. For example, if in a 40-question reading section, a student went back to reread the passage on 30 questions, their score would be: 30/40×100=75%.

In some embodiments, a "test equanimity" value is also calculated and displayed in the GUI. In some embodiments, test equanimity measures a student's ability to recover after a difficult question or questions and their ability to stay calm throughout the test. There are different reasons a student gets upset during an exam. The two most common are a difficult question or anxiety around a specific question type. In some embodiments, the system can determine when exactly during an exam a pulse spikes, and the system can also determine which question the student is viewing at that time to determine what is causing their anxiety.

In some embodiments, the system measures the student's ability to stay calm during difficult questions. In some embodiments, 75% of the score is calculated from how the student does on a question AFTER they spend a minute on a question. In some embodiments, the system measures time per question as each question is on a different screen, so the system can tell how long a student is working on a question by how long they spend on that screen. For example, if they spend a minute on question 5, how they do on question 6 is a factor. If they spend over a minute on questions 5 and 6, how they do on questions 6 and 7 are factors. If they spend over a minute on 10 questions, and they get 8 of the next ten right, then they get 8/10×0.75=60 points.

In some embodiments, the system measures for any specific anxieties. 75% of the score, as described above, is calculated from how a student does AFTER a difficult question. In some embodiments, the remaining 25% of the score is calculated from pulse, which the system measures through the computer's camera. In some embodiments, this is accomplished by measuring small movements of the head of the test taker (a person's head, around the vein area, moves in relation to their blood pressure, which a computer camera can detect). In some embodiments, the system determines whether the student's pulse ever rises more than 10% of its pre-test rate at any time during the test. In such embodiments, if it does, the system removes 5 points each time. If it never goes up more than 10%, the student gets a value of 25 out of 25. If for any reason, the system does not get a good pulse reading, the system will default to give the student 25 points for this section. In some embodiments, the equation for test equanimity can be given as follows:

$$\text{Test Equanimity} = (75 \times ((\text{number of questions right after spending more than 1 minute on a question}) \div (\text{total number of questions directly after a question that took more than 1 minute})) + (25 - 5m).$$

In the above equation, m represents the number of times a pulse spikes. In some embodiments, it cannot be greater than 5. For example, if the student spent over a minute on 10 questions, and on the following questions, they got 8 of 10 correct. In addition, their pulse jumped twice. Then they get 60 for the first part, plus 15, for a total score of 75%.

In some embodiments, a "time awareness" value is calculated and displayed in the GUI. In some embodiments, time awareness measures how a student uses their time. As explained earlier, each question is on a different screen, so the program can tell how long a student spends on a question or group of questions.

In some embodiments, 75% of the score is how they paced themselves through the first 80% of a section. In some embodiments, 25% of the score is determined by whether they finished the section. In some embodiments, this is calculated independently for each section. In such embodiments, the average is then taken to calculate the total time awareness score. For example, in some embodiments the time awareness score can be calculated as follows:

$$\text{Time Awareness} = (75 \times (\tfrac{2}{3} \times \text{of the allowable time in the section}) \div (\text{time spent on the first 80\% of the questions in the section})) + (25m).$$

In the above equation, m=1 if the student finished the section and 0 if they did not. In some embodiments, the first part of the question has a maximum of 75. For example, if a student spends 50 minutes of a 60 minute section on the first 80% of a section, and finishes, they get: 75×(40/50)+25=85% for that section.

In some embodiments, a "test readiness" value is also calculated and displayed in the GUI. In some embodiments, test readiness value is based on a target test score, and is calculated as follows: In some embodiments, 70% of the test readiness value is calculated dividing the student's actual test score by the target score (max is 1). If there is no target score, then the default is to use 75% of the max score as the target score. In some embodiments, 15% of the test readiness value is derived by averaging the calculated values of Grit, Vertical Fluidity, Test Equanimity and Time Awareness. In some embodiments, the last 15% of the test readiness value is derived by averaging how the student performed on questions of difficulty levels 2-5.

For example, if a student takes a mock SAT exam and has the following scores and performance metrics: SAT score: 1350, Target score: 1450, Grit—70%, Vertical Fluidity—60%, Test Equanimity—70%, Time Awareness—70%, % of Difficulty 2-5: 80%, Score/Target score=1350/1450=93%, Avg. of Grit, et al.=70%, and Difficulty 2-5=80%, then the overall test readiness score can be calculated as the following: Test Readiness=(0.93×0.7)+(0.7×0.15)+(0.8×0.15)=0.88=88%.

In some embodiments, test readiness can be displayed as visuals in a GUI, e.g., a bar graph that fills the entire box horizontally. In some embodiments, a chart is also presented to the user. In some embodiments, the chart shows at what time within a section a student answered every question and if they answered it correctly or incorrectly. In some embodiments, the chart also shows each time the student went to a new slide (every question is on a different slide, so when a student goes to a new slide, they are going to a new question). In such embodiments, this lets the system know if a student is checking their work at the end of a section. If after a student answers the last question, they stay on the same slide, then they are not checking their work. If they do go to a new slide, they most likely are. In some embodiments, a slide or answer is displayed by a colored dot on the chart. If the user scrolls with their cursor over one of the colored dots, the question the student was looking at is shown.

In some embodiments, the chart also shows pulse and blinks throughout the section, so the system can see if a student's pulse jumps, and what they were looking at when it jumped. As explained earlier, the system measures pulse by measuring slight vibrations in the head of the student through the computer camera. The computer camera also can tell when a student blinks, which is also displayed.

In some embodiments, the chart also lets the user zoom in on a period of time, e.g., from minute 5 to minute 10. In some embodiments, a student receives a different chart for each section of the exam. For example, the SAT has 4 sections, so a student receives a chart for each of those sections.

In some embodiments, a timing section is displayed in the GUI. In such embodiments, this section shows how much time a student spent on each question. For example, this includes—on reading sections—how much time they spent reading each passage. It also shows the average time that other test takers have spent on each question and each reading passage. In some embodiments, each passage and each question is on a different screen, so the system can measure how long a student spends on each screen as a determination of how long they spent on that passage or question.

In some embodiments, an eye tracking section is displayed in the GUI. In such embodiments, eye tracking shows valuable information, such as whether a student reread a reading passage when answering questions about that passage, or if they got the question right or wrong. The system tracks eyes using two methods. In one method, the passage is always on an earlier screen than the questions, and system measures automatically whether a student goes back to that previous screen while doing the questions. In another method, the passage and the question are on the same screen, but the passage is on the left side and the question is on the right. When this happens, the screen is split 40/20/40 (left/center/right), as previously described above. According to various embodiments, the system tracks eye movement through the computer's camera to tell if a student is looking at the passage on the left after reading the question on the right. In some embodiments, when a student first logs on to take a test, the system first calibrates their eye movement through machine learning techniques.

In some embodiments, a video section is displayed in the GUI. In such embodiments, the video section shows a video of the student taking the test. This lets the student or the teacher see important information about the test performance, e.g., if the student left the testing area during a section.

In some embodiments, an answer key section is also displayed in the GUI. In such embodiments, the answer key shows the correct answer for every question and the student's answer for every question. It also shows the level of difficulty for each question. In some embodiments, the answer key includes video explanations for each question.

In some embodiments, a full test section is also displayed in the GUI. In such embodiments, this section displays the full test that the student just took, including all questions and answers, and including which answers the student chose and whether the answers are right or wrong. In addition, in some embodiments the difficulty of the question is also displayed.

In some embodiments, in order to accurately measure certain performance metrics, such as time spent on a question or whether the student reread a passage, the test taking user interface must be specially modified to allow the system to capture the desired metrics. In some embodiments, the test user interface must show students one question at a time only. In some embodiments, a navigation pad that shows how many questions are in the section and which have been answered and which have not been answered (this is done by color) is also displayed. In some embodiments, there is also a timer in the graphical user interface, which is counting down the time remaining in the section, as well as a video of the student. In some embodiments, one advantage of the video is to ensure that the student is within range of the computer's camera. As mentioned above, in some embodiments, at the beginning of a test before a student gets to the actual exam, the student can perform a short calibration test by clicking on dots around the screen. This is done to calibrate the student's eye movements with the camera. In some embodiments, the student then sets their target score for the exam before beginning the exam.

In some embodiments, the stimulus session is a test taking session. In some embodiments, the cues and reactions include one or more of the following: pulse, eye blink rate, eye movement, and pupil dilation. In some embodiments, the stimulus session includes test questions, each test question being tagged with a difficulty level. In some embodiments, post-processing the recorded cues and reactions includes calculating pacing throughout the stimulus session. In some embodiments, providing feedback includes presenting a graphical representation of the user's performance during the stimulus session. In some embodiments, the method further comprises optimizing the feedback provided using a predictive artificial intelligence model.

Figure 2:
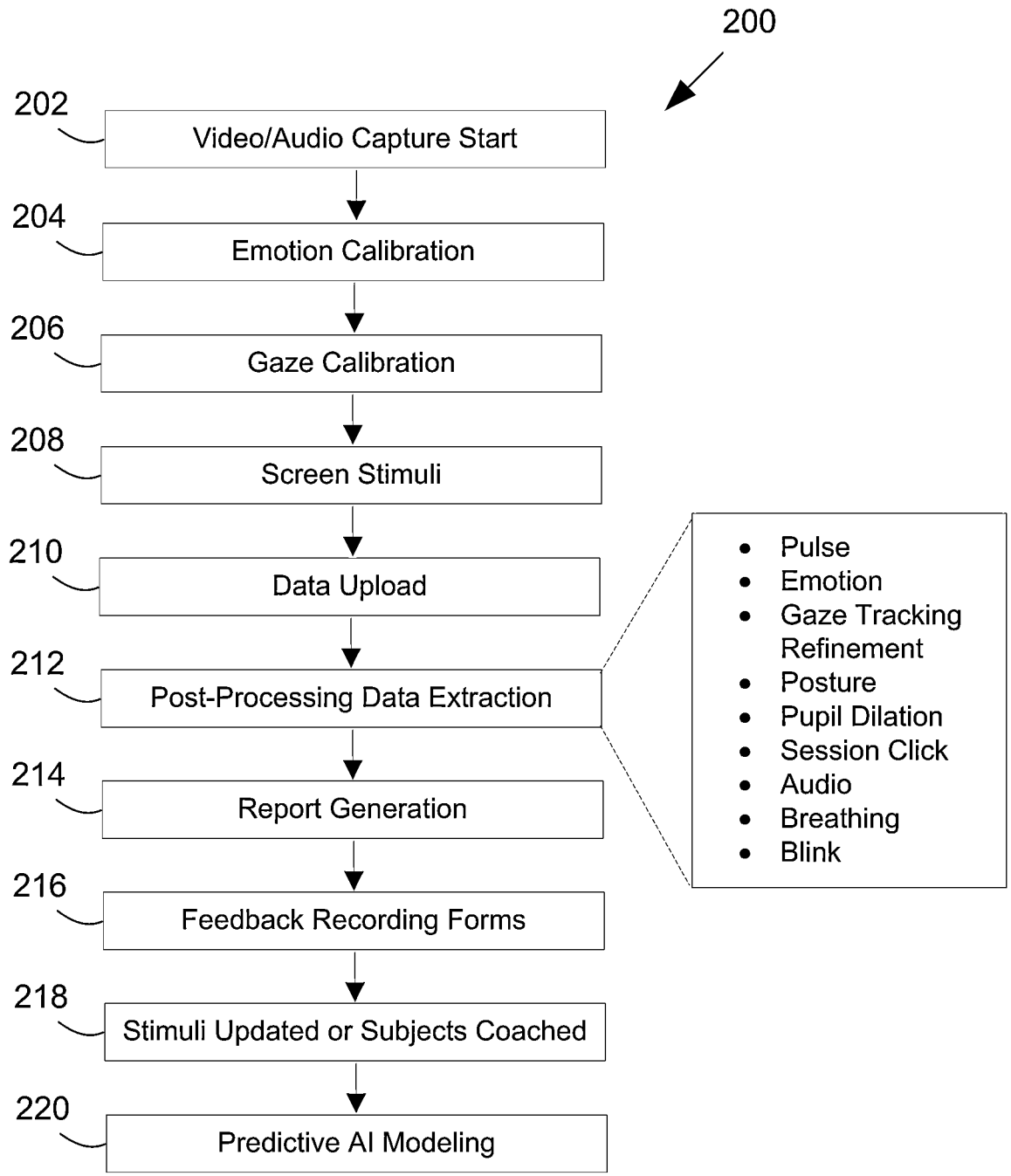
FIG. 2 shows a flow chart of another method for educational analysis optimization, in accordance with embodiments of the present disclosure.

As described above, FIG. 1 illustrates one method for educational analysis. FIG. 2 illustrates another method for education analysis. FIG. 2 shows a flow chart of another method for educational analysis optimization, in accordance with embodiments of the present disclosure. Method 200 is an example of a more detailed method for educational analysis optimization. At step 202, a user initiates a test. In some embodiments, the user, using a personal computing device with a camera, connects to the Internet and navigates to the test start page using a web browser. In some embodiments, the web browser automatically loads all the source files to create the page on which a Javascript program utilizes for data capture and gaze analysis. In some embodiments, the user gives permission for the Javascript program to access the camera. The Javascript program will start recording the video stream. In some embodiments, a unique session ID for each test and user is given via one or more of the following: a cookie, a tracked by IP, a unique browser fingerprint, or a session ID maintained in the web server's memory.

At step 204, baseline is established and cues for emotion are calibrated. In some embodiments, the user is displayed stimulating material, such as a video or video game, to illicit facial responses for emotions such as happiness, relaxation, stress, or intense focus. In some embodiments, the camera video stream is saved during this game for later use, as described in further detail with regard to step 212. In some embodiments, timestamps are accurately recorded to ensure server side processing of the video will automatically align with emotions.

At step 206, cues for gaze are calibrated. In some embodiments, the user is shown a page with 8 dots arranged around the page and a video showing their face in a bounding box to help them keep their face centered in the cameras field of view. In some embodiments, directions are shown to the user asking them to click each dot 5 times. In some embodiments, the dots provide instant feedback for each click by changing to a different color. In some embodiments, after being clicked 5 times each dot disappears. In some embodiments, once all the dots have been clicked and then disappeared a ninth dot is shown. Once this is clicked, further directions are shown asking the client to stare intently at the last dot but not move the mouse for 5 seconds. According to various embodiments, the clicks recorded are then used to calibrate triangulation formulas used to calculate the area of the screen the user looks at.

At step 208, the user is shown the screen stimuli. In some embodiments, the stimuli can be standardized tests for college admissions. During the stimuli, biometric data is constantly recorded to understand important information, such as what the user reads, how much the user reads, and the corresponding emotional and physical reactions during reading. In addition, in some embodiments, important information includes understanding emotional and physical reactions to advertising material, videos, graphics, and pictures, as well as the types and duration of the videos/graphics/pictures. As with step 204, in some embodiments, the captured video and gaze tracking data may be saved for later use in step 212.

At step 210, the user finishes viewing and or interacting with the screen stimuli such as tests, reading, watching videos, looking at images and pictures. In some embodiments, the video recording is then stopped and uploaded to the server. In some embodiments, the video is uploaded with the unique session ID and other data already uploaded and or recorded during this session. In some embodiments, the user is thanked and, if relevant, is advised that the data analysis could take at least a few moments and they will be contacted if needed.

At step 212, all video and data is uploaded to the server and post-processed for data extraction. In some embodiments, if the system has multiple servers available the system can copy the video to each server and initialize each program for extracting the biometric data desired. If there is only one server, then the system can either initialize all the programs at once, or run them sequentially. In some embodiments, if all the programs have been combined into one master program then the system can run one or more copies per server in either sequential or parallel processing mode. According to various embodiments, regardless of the implementation the extracted data is inserted into a database. Tables in the database use session IDs to separate the test results of multiple tests. In some embodiments, the inserted data is stored in either one of two formats: 1) frame by frame extractions, where the extracted data is inserted with the timestamp, e.g., inserted as estimated pulse, frame #, and time stamp, or 11) changes in condition, e.g., from smile to neutral, which gets inserted as frame #, data such as facial expression, and time stamp. According to various embodiments, the accurate time stamps allow the system to generate reports in step 214. According to various embodiments, all of the data gathered and generated in 204, 206, 208, 212 is used in 220.

At step 214, a report is generated. In some embodiments, the report generation is done via two methods. One method is direct graph generation, which is good for printing. The other method uses interactive Javascript graphs, which allow instantaneous research about what data was used to generate the graph at the instant the pointer of the computer is hovering over. In some embodiments, the graphs are drawn with a timeline on the horizontal, or x, axis and the value of the variable in the vertical, or y, axis. In some embodiments, switching the axes can also be done if needed by clicking a switch view option. In some embodiments, the switch view option changes the Javascript graphing libraries references from y to x and x to y, using a temporary variable to keep the transition from one axis to the other axis from overwriting the other before the transition can complete.

In some embodiments, the direct graph method uses standard image creation libraries available in popular web programming languages such as PHP or Python. In some embodiments, the rest of the data is shown as standard text. In some embodiments, the data displays the words read vs not read, displays how many times a word was read and not read, and/or creates heat maps. In some test implementations, the display of questions and answers to the test is displayed in the order they are viewed on the test with the time they were answered.

In some embodiments, if a Javascript graph is used, then the questions are displayed by the time they were answered. In some embodiments, the question is displayed more than once if the user changed answers. This type of data in combination with biometric data is very useful in understanding where students are struggling. In some embodiments, some data is displayed by a line on the graph such as pulse rate and pupil diameter. In some embodiments, other data such as emotions are displayed by bubbles or other shapes that scale based on intensity of the reading. For example, blinks are displayed as bubbles, where the longer a blink takes, the bigger the bubble. Multiple long blinks might indicate a person was sleepy, whereas steady quick blinks might indicate the person was fully awake and comfortable. In some embodiments, answers show up on the graph as simple symbols such as squares. In some embodiments, if the user hovers over the symbol, it will display data about what word was read, pulse, emotions, and/or write or wrong answers. In some embodiments, a graphic data display is shown by heat map thumbnails based on time in order to coordinate eye movement chronologically with biometric data. In some embodiments, video display is facilitated by embedding metadata in the video that describes each segment of the video. In some embodiments, videos are graphed by overlaying thumbnails extracted from the video into the Javascript graph and put on the timeline while displaying the user biometric data.

At step 216, feedback forms are generated. In some embodiments, this includes recording the feedback given to users or the creators of the content. In some embodiments, the recorded feedback is used for AI training in step 220. In some embodiments, the feedback form is customized based on the needs of the content creator or other parties. In some embodiments, the form will have a text area and file upload ability. In some embodiments, the form might be enabled to capture video from the webcam. According to various embodiments, some feedback is given directly to users for various purposes, e.g., for coaching on test taking, trauma coaching, reading safety manuals, or other required reading, or watching videos that are required. According to various embodiments, the system can tell if someone is actually reading or watching. In some embodiments, other data can be used for content creation or content presentation professionals such as writers, video makers, marketers, speech writers and or speech readers, actors etc. In such embodiments, based on user experiences, content creators or content presenters can refine their materials and or presentation to illicit the emotional and biometric feedback they are seeking. In some embodiments, the feedback data given can be text, graphics and or video or any mix.

At step 218, feedback is displayed to users, content creators and or content presenters. In some embodiments, feedback is displayed via a webpage or app that will also record their reactions to the feedback itself (using techniques described in steps 204, 206, and 208). In such embodiments, the recorded reactions to the feedback can then be submitted as data itself and be processed using techniques described in step 212, and also to be used for AI training in step 220.

At step 220, the system seeks to coach the coaches and or advise the advisors by observing the complete cycle of stimuli eliciting responses from users and feedback to users, content creators and content presenters. In some embodiments, observing the cycle causes refinement which will create new responses. In some embodiments, the AI uses predictive modeling using sample data consisting of feedback marked up to include success and failure metadata. In some embodiments, the markup of the sample data is done by people interpreting the results. However, in other embodiments, the markups are also done using AI trained to markup sample data. As the models become increasingly more accurate, the coaching and advice follows suit. In some embodiments, predictive AI modeling monitors the subject's response to stimuli and feedback, and/or stimuli updates and the subject's new response to stimuli and predicting outcomes. In some embodiments, the predictive AI model generates feedback based on previous human feedback and inferred results of the subject's new response to stimuli.

Figure 3A:
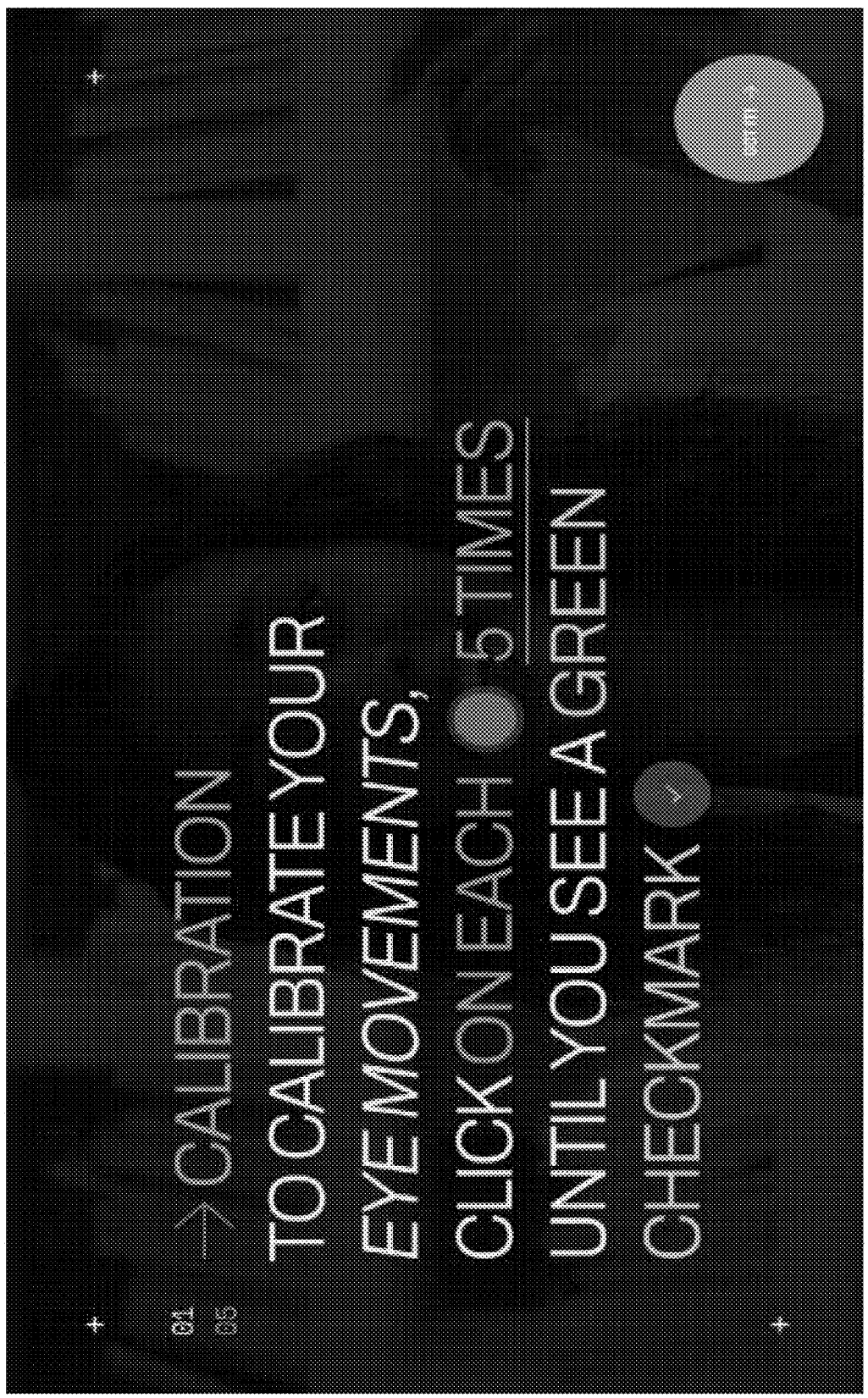
FIGS. 3A-3D, FIGS. 4A-4B, 5,6, 7, 8, and 9A-9F depict screenshots of an example graphical user interface, in accordance with embodiments of the present disclosure.
Figure 3B:
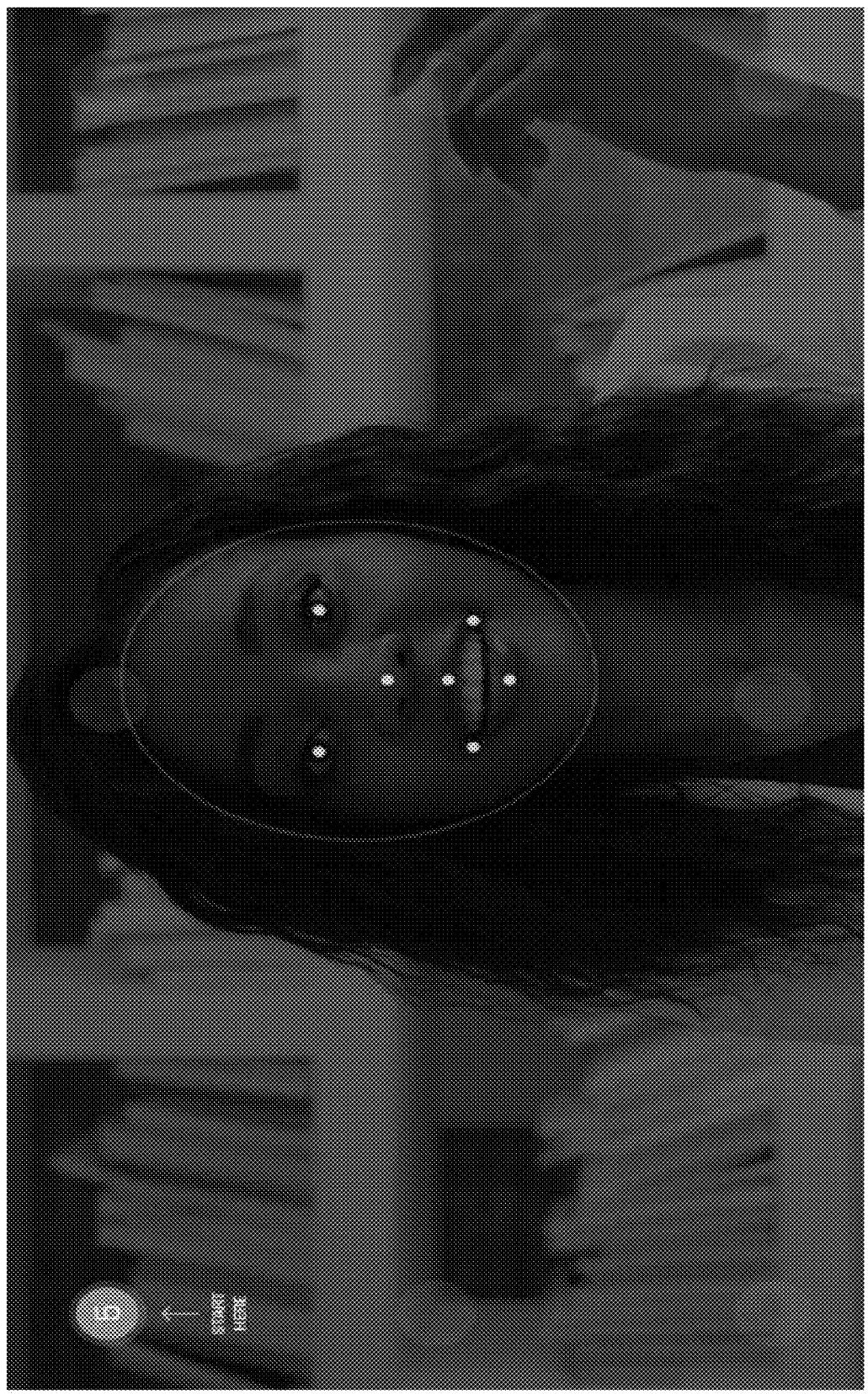
Figure 3C:
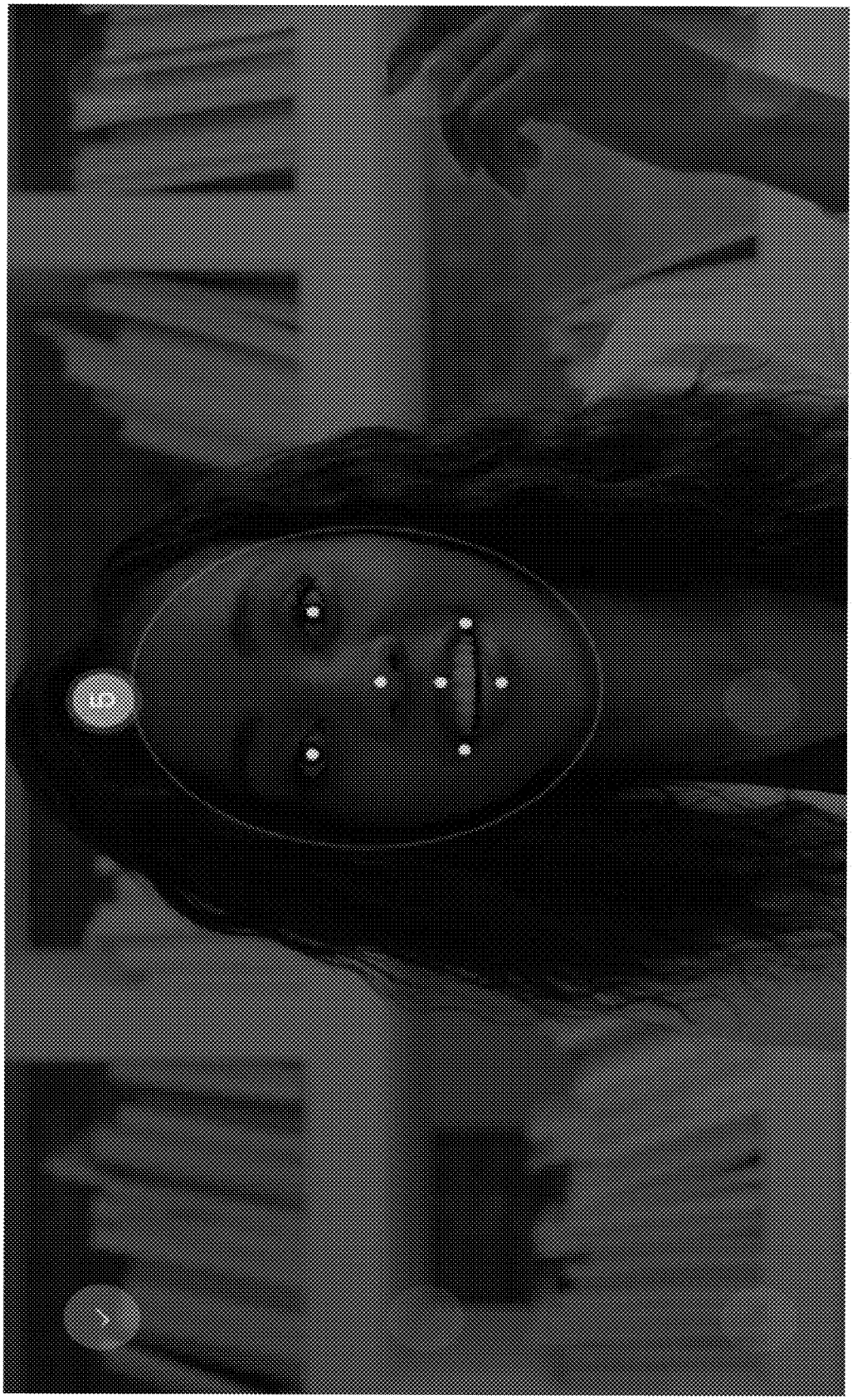
Figure 3D:
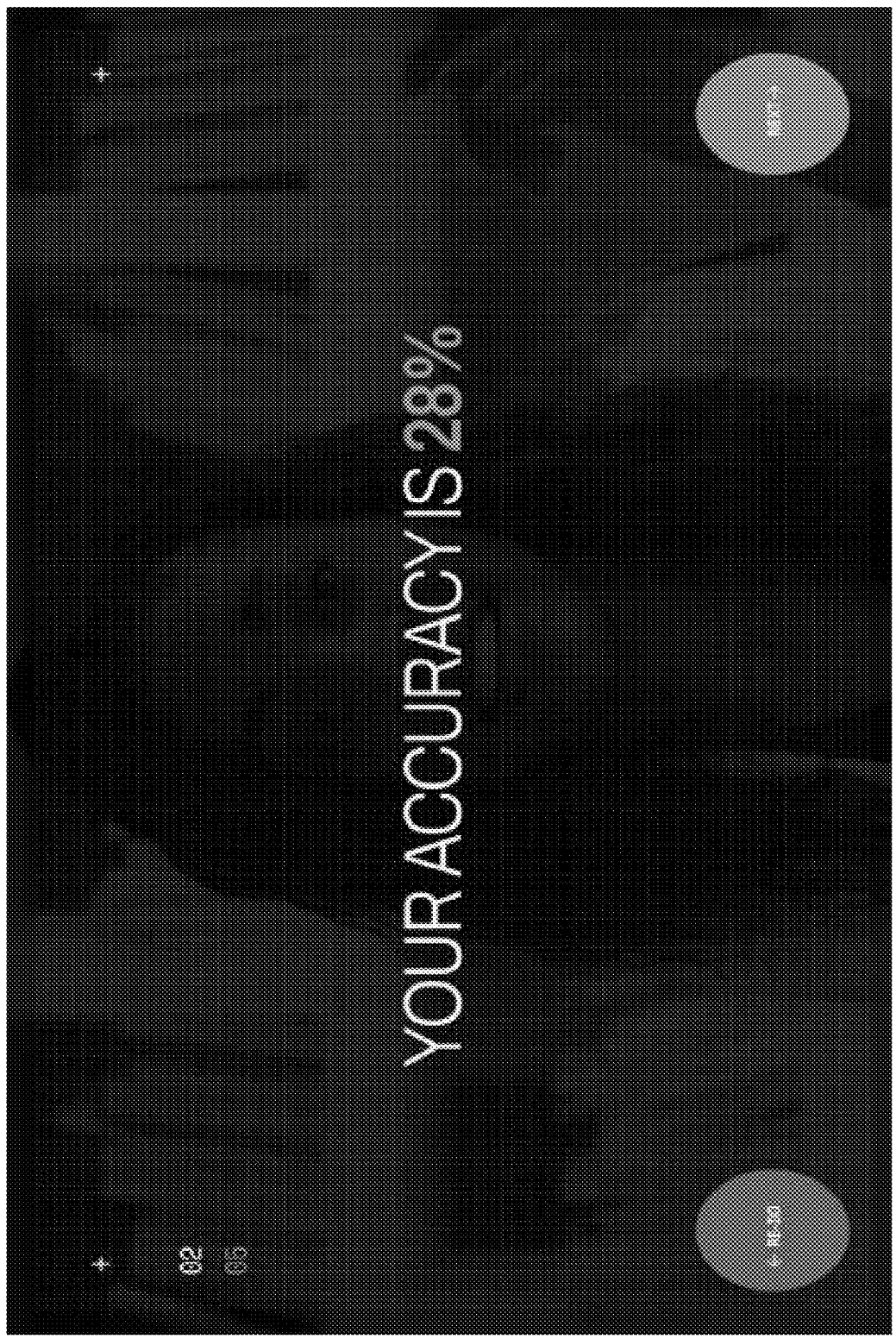
Figure 4A:
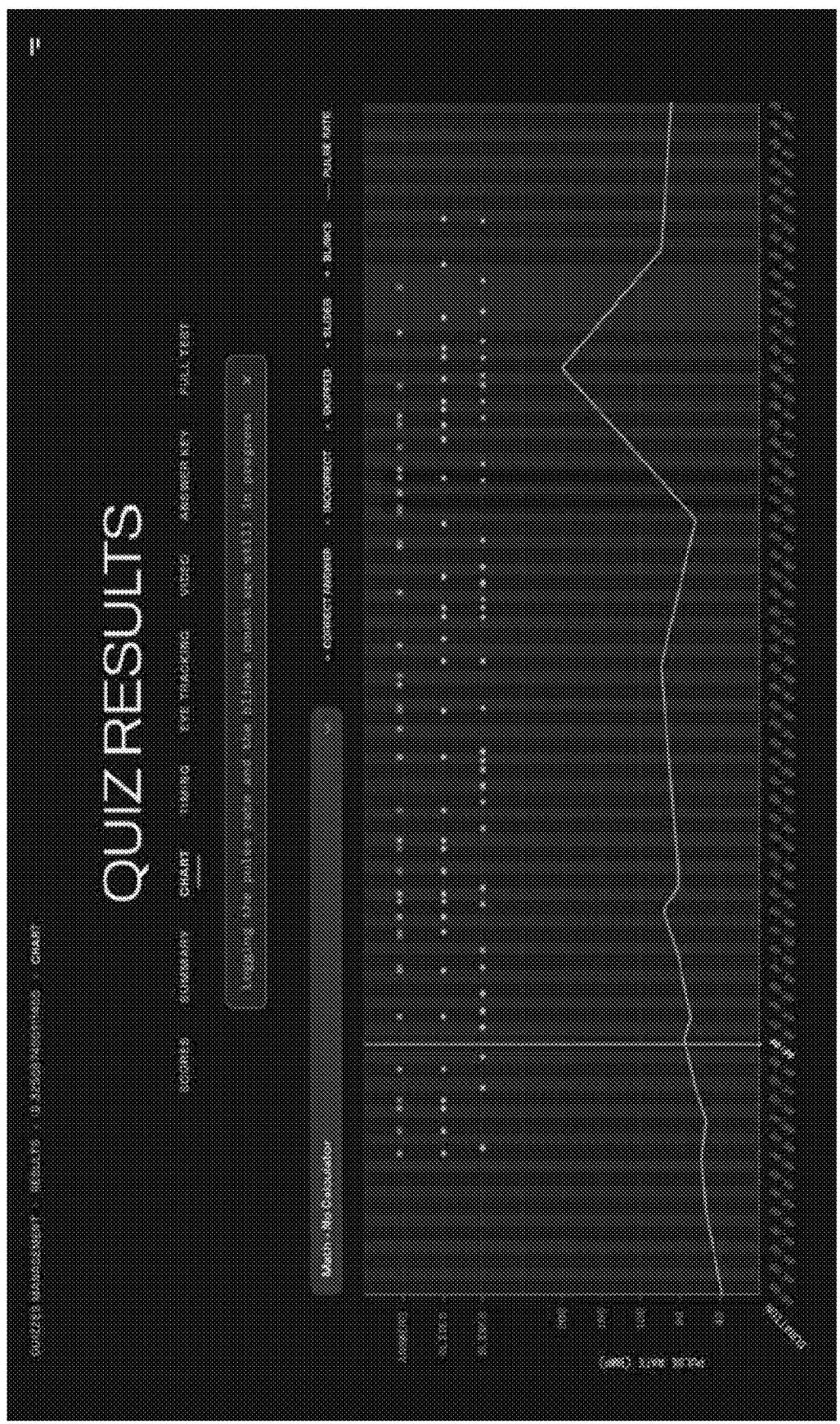
Figure 4B:
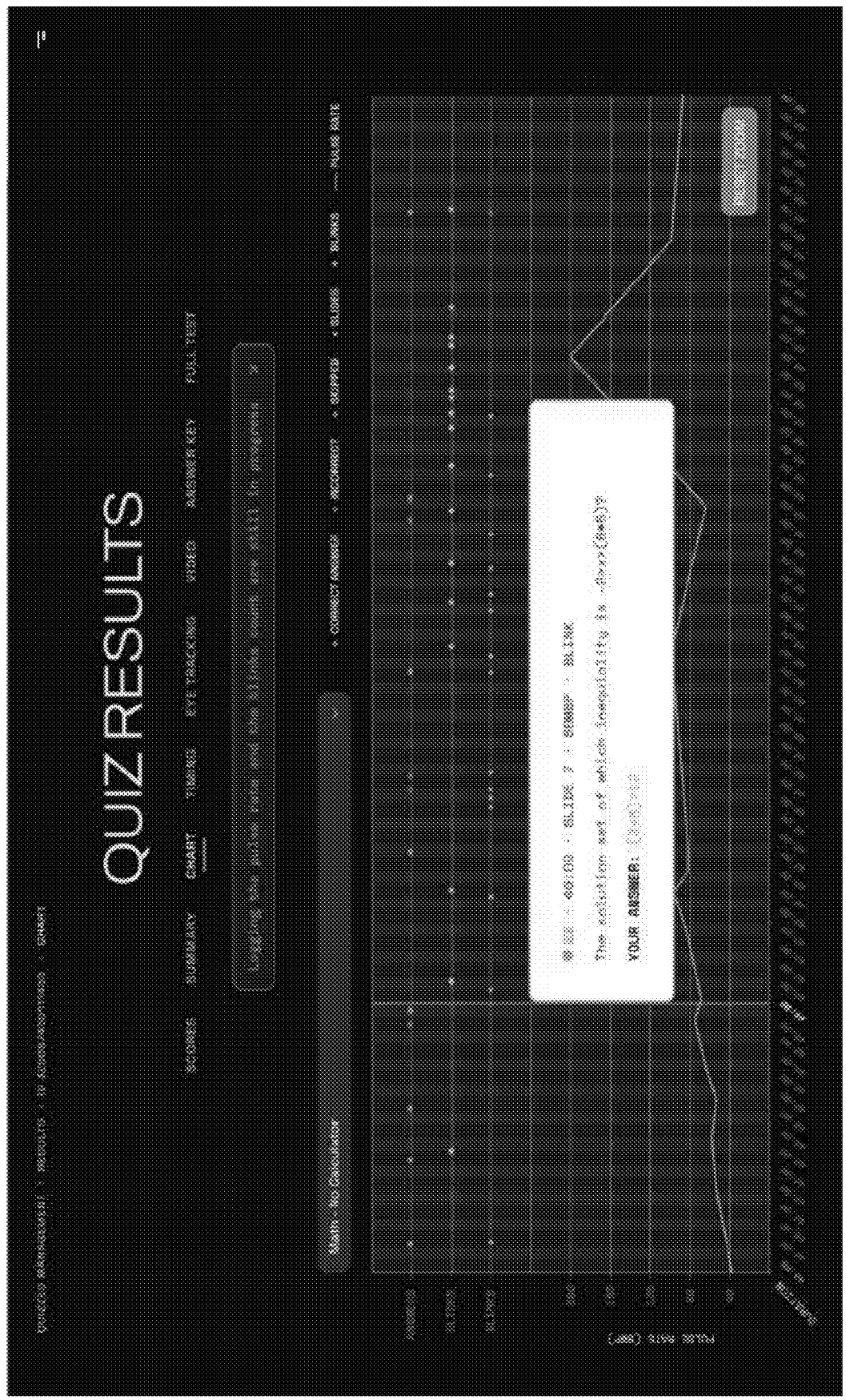
Figure 5:
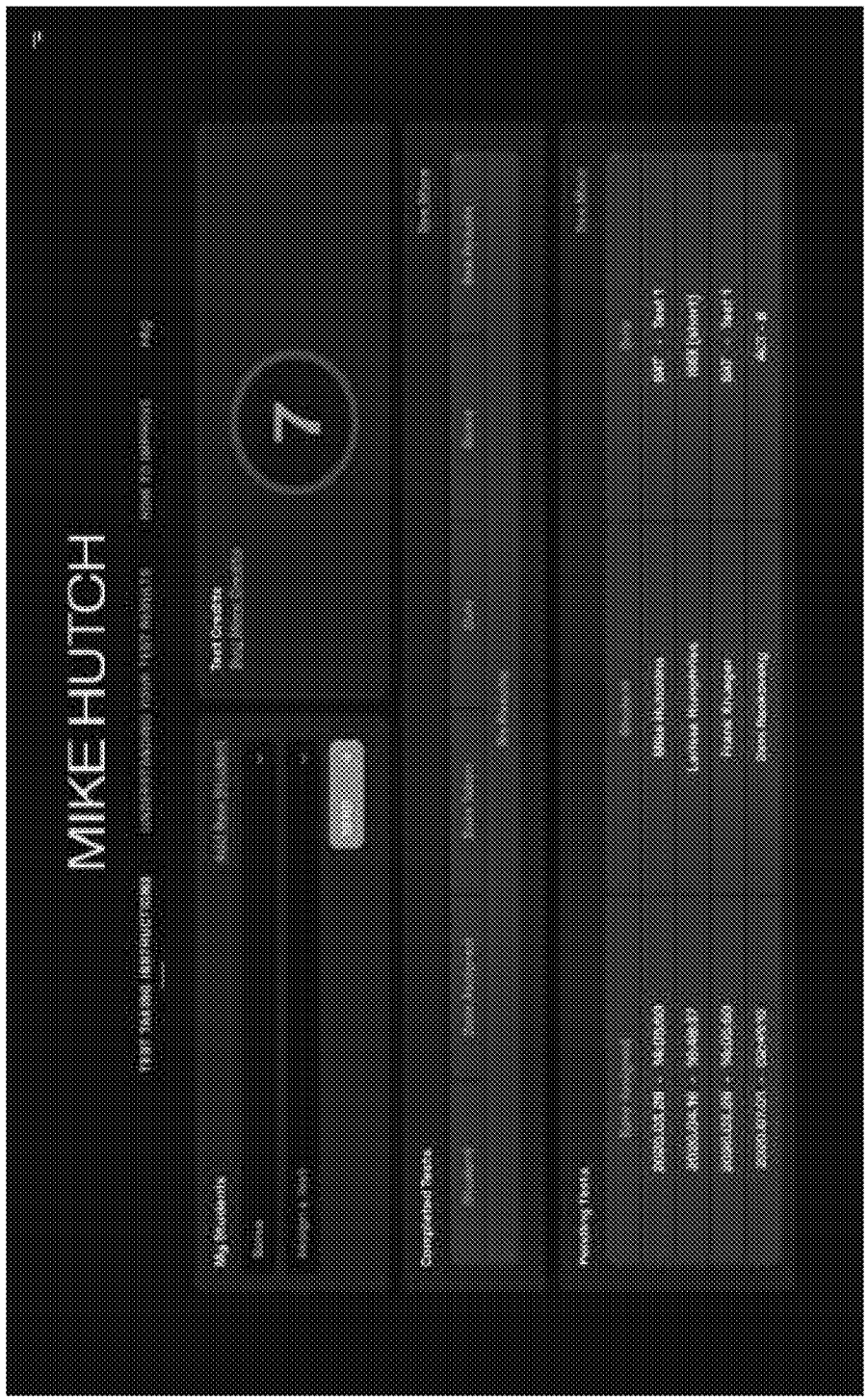
Figure 6:
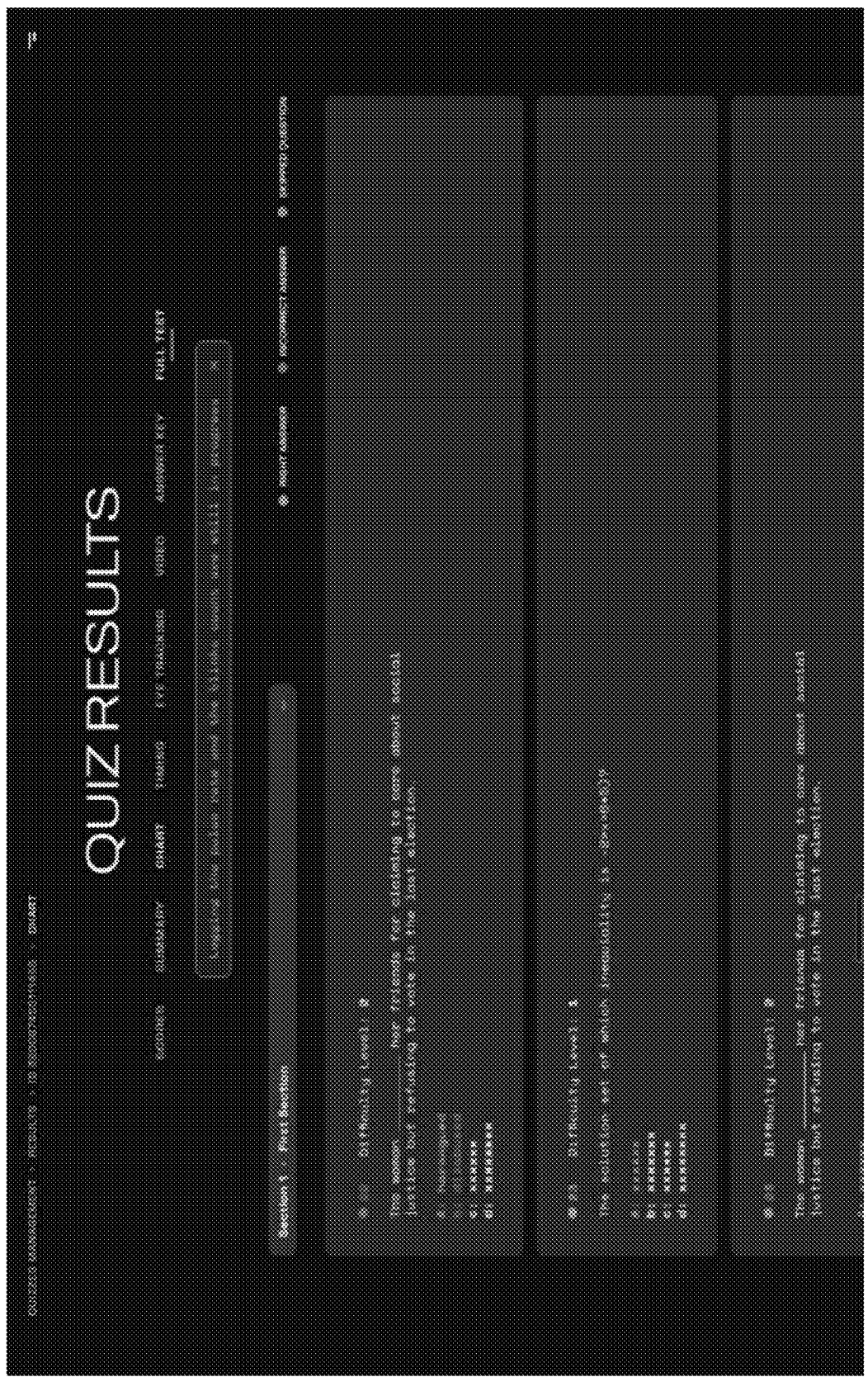
Figure 7:
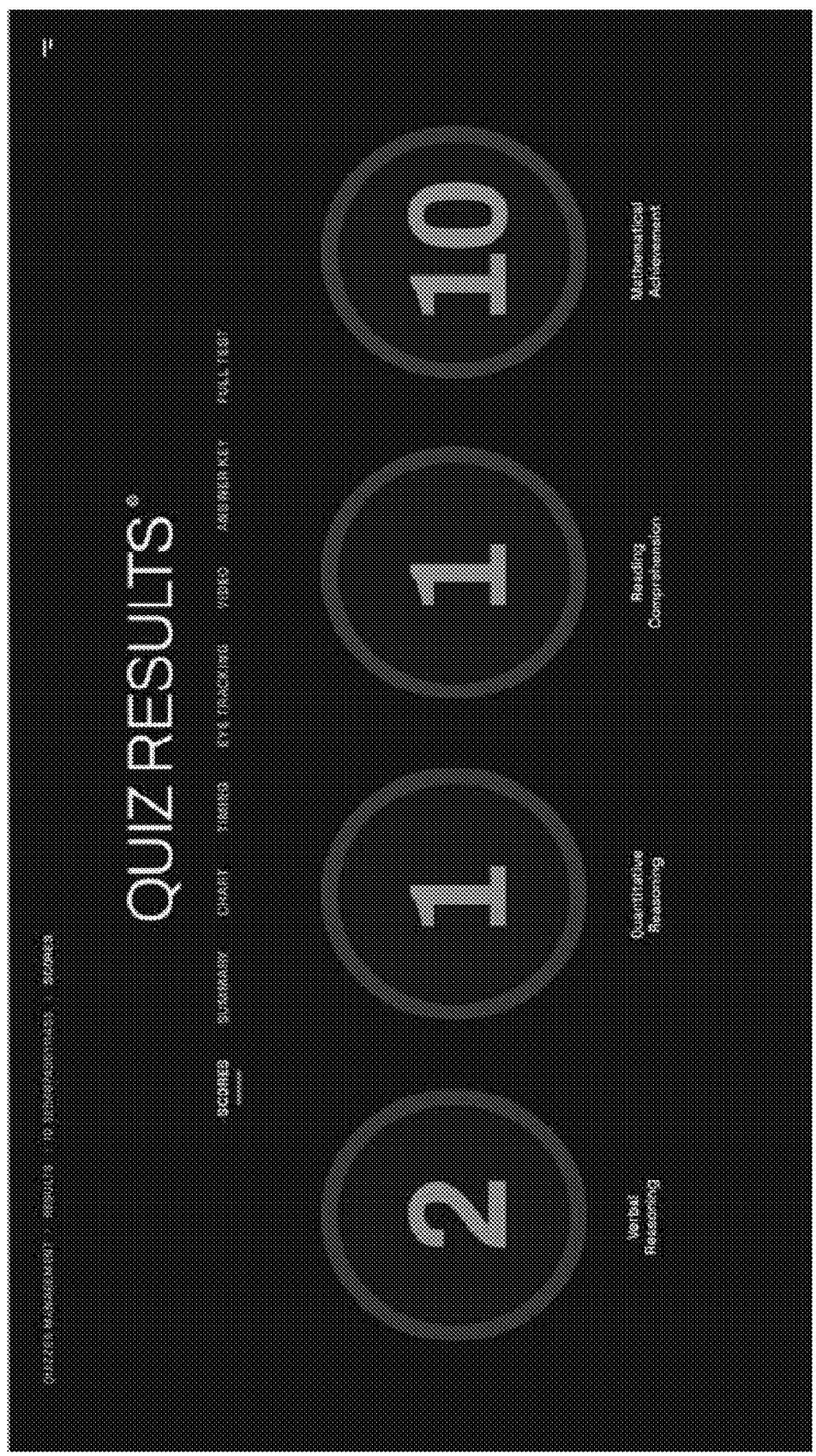
Figure 8:
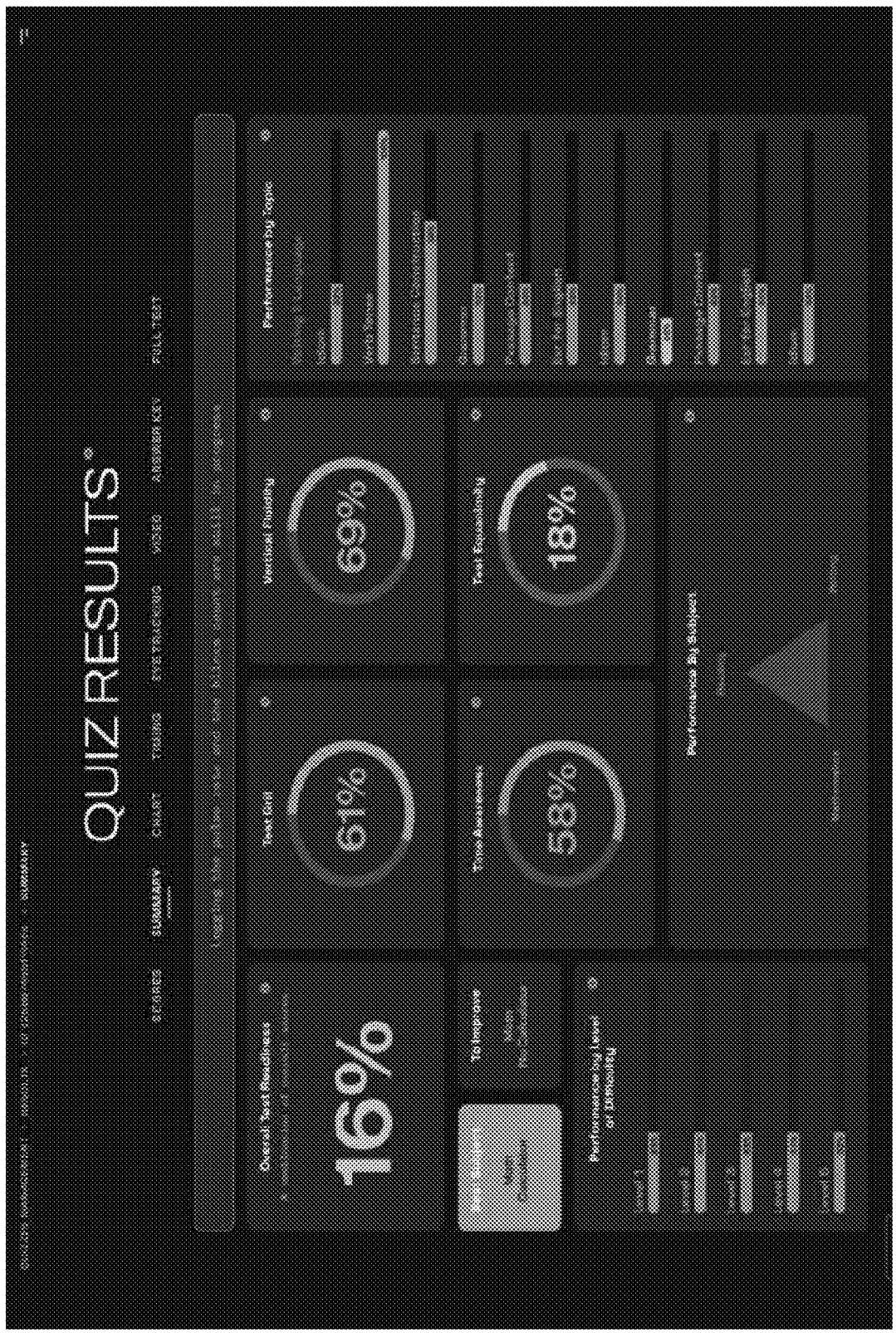
Figure 9A:
Figure 9A:
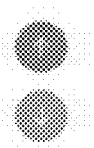
Figure 9B:
Figure 9B:
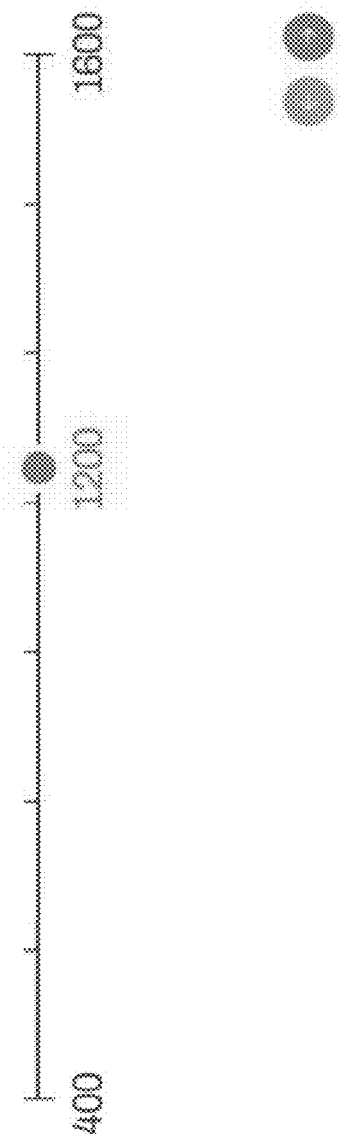
Figure 9C:
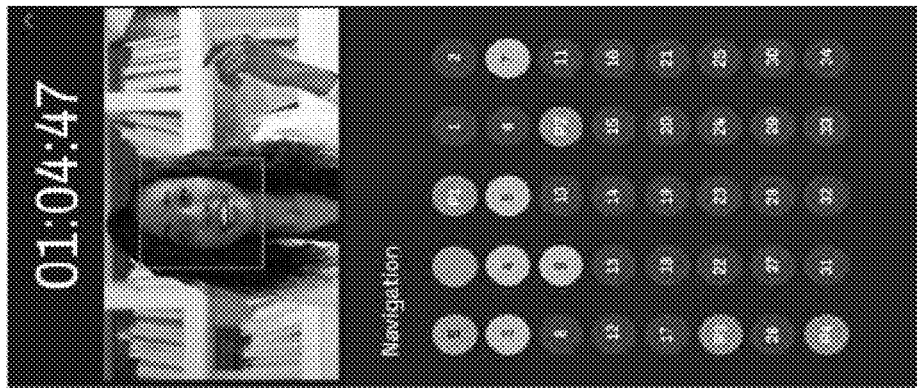
Figure 9C:
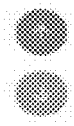
Figure 9D:
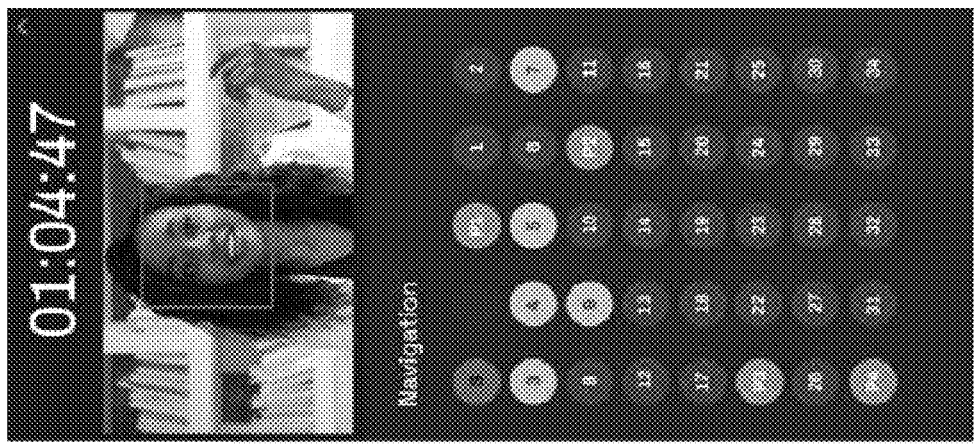
Figure 9E:
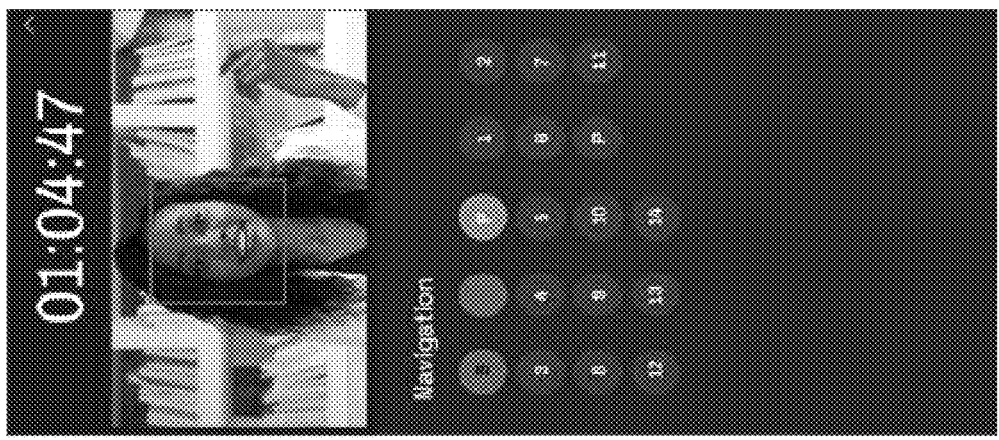
Figure 9F:

One important aspect of the present disclosure is the graphical user interface (GUI). The system utilizes a unique GUI for engaging with a student. FIGS. 3A-9F depict screenshots of an example graphical user interface. Each figure shows a screenshot of different screens in the interface. FIG. 3A shows an example calibration screen with instructions. FIGS. 3B-C show example calibration screens as the system is identifying facial features. FIG. 3D shows an example calibration screen showing the results of the calibration. FIGS. 4A-4B show an example Chart section, as mentioned above, with quiz results. FIG. 5 shows an example dashboard. FIG. 6 shows an example Full Test section, as mentioned above. FIG. 7 shows an example Scores section, as mentioned above. FIG. 8 shows an example Summary section, as mentioned above. FIGS. 9A-9F show different screenshots of a session where the student is taking the full exam. FIG. 9F specifically shows a mid-test break timer.

Figure 10:
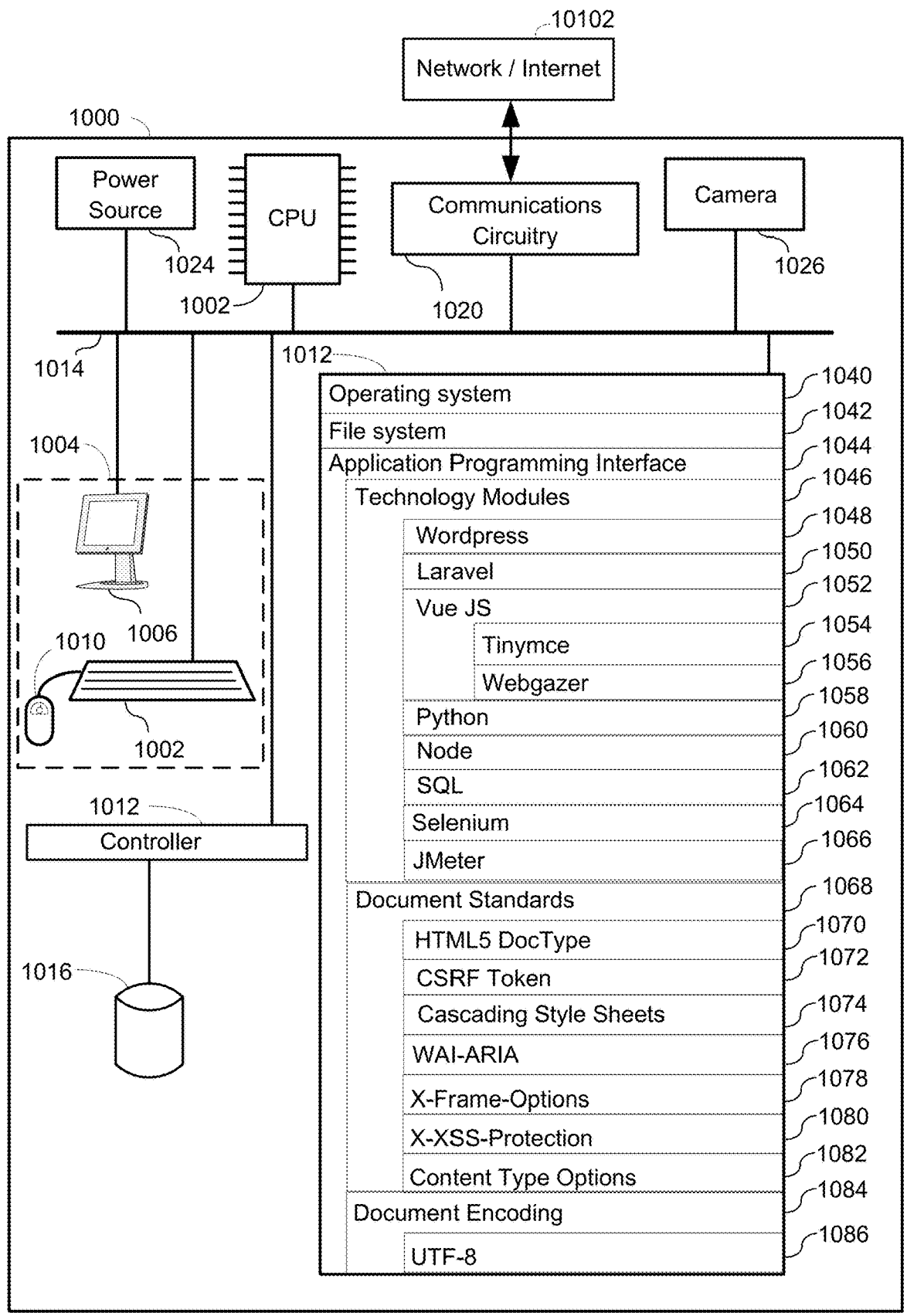
FIG. 10 shows one example of a system architecture, in accordance with embodiments of the present disclosure.

FIG. 10 is a block diagram illustrating an example of a computer system capable of implementing various processes described in the present disclosure. The system 1000 typically includes a power source 1024; one or more processing units (CPU's) 1002 for executing modules, programs and/or instructions stored in memory 1012 and thereby performing processing operations; one or more network or other communications circuitry or interfaces 1020 for communicating with a network 1022; controller 1012; and one or more communication buses 1014 for interconnecting these components. In some embodiments, network 1022 can be another communication bus, the Internet, an Ethernet, an Intranet, other wide area networks, local area networks, and metropolitan area networks. Communication buses 1014 optionally include circuitry (sometimes called a chipset) that interconnects and controls communications between system components. System 1000 optionally includes a user interface 1004 comprising a display device 1006, a keyboard 1008, and a mouse 1010. In addition, system 1000 includes camera 1026, which may or may not be a webcam or a built-in computer camera. Memory 1012 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 1012 may optionally include one or more storage devices 1016 remotely located from the CPU(s) 1002. Memory 1012, or alternately the non-volatile memory device(s) within memory 1012, comprises a non-transitory computer readable storage medium. In some embodiments, memory 1012, or the computer readable storage medium of memory 1012 stores the following programs, modules and data structures, or a subset thereof:

- an operating system 1040 that includes procedures for handling various basic system services and for performing hardware dependent tasks;
- a file system 1044 for storing various program files; and
- an application programming interface 1044 for implementing software functions.

Application Programming Interface 1044 may also include the following submodules, or a subset thereof:
- Technology modules 1046 for executing program instructions;
- Document standards 1068 for determining the correct format for communication with other devices; and
- Document encoding 1084 for encoding electronic communications. UTF-8 1086 is the preferred encoding for web pages.

Technology modules 1046 also include the following submodules, or a subset thereof:
- Wordpress 1048 for developing a framework for a website. This can be integrated into a test-taking application. It passes information entered on the website via a JSON packet;
- Laravel 1050 for developing a PHP framework that manages roles, accounts, and pages. This makes developing web apps easier. Includes website tools, e.g., login;
- Vue JS 1052 for developing a frontend framework, such as drawing the display. Vue JS is responsible for user interface (UI) activities; Vue JS may also include the following submodules
    - Tinymce 1054 for creating tests and other functions, e.g., formatting questions or paragraphs and display;
    - Webgazer 1056 for recording of screen and data using camera as input. It is used for face and eye analysis, using point-to-point triangulation with a user's pupils, and implemented using Javascript. Webgazer 1056 detects microvariations, such as pupil dilation and forehead pulse, which are undetectable to the human eye;
- Python 1058 for implementing AI models for camera and movement detections;
- Node 1060 for supporting Vue JS 1052 to run seamlessly and have plugins for it which is useful for camera and other movement detection. Node 1060 supports Vue JS and flow data to Python 1058 using shell script on a server;
- SQL 1062 for storing data and activities in a database;
- Selenium 1064 for generating automated testing scripts; and
- JMeter 1066 for load testing and benchmarking of a server.

Document Standards 1068 also includes the following submodules, or a subset thereof:
- HTML5 DocType 1070 for providing headers for HTML5 websites;
- CSRF Token 1072 for generating a unique token;
- Cascading Style Sheets 1074 for describing the presentation of a document written in a markup language;

WAI-ARIA 1076 for making web content and applications more accessible. It especially helps with dynamic content and advanced user interface controls;

X-Frame-Options 1078 for indicating whether or not a browser should be allowed to render a page in a frame or iframe. This is often used to ensure that content is not embedded into other sites;

X-Xss-Protection 1080 for preventing XSS attacks by implementing a header that lets domains toggle on and off the "XSS Filter" of certain browsers; and Content Type Options 1082 for disabling MIME-sniffing for particular HTTP responses.

Each of the above identified elements may be stored in one or more of the previously mentioned memory devices, and corresponds to a set of instructions for performing a function described above. The above identified modules or programs (i.e., sets of instructions) need not be implemented as separate software programs, procedures or modules, and thus various subsets of these modules may be combined or otherwise re-arranged in various embodiments. In some embodiments, memory 1012 may store a subset of the modules and data structures identified above. Furthermore, memory 1012 may store additional modules and data structures not described above.

Although FIG. 10 shows a "biometric analysis system," FIG. 10 is intended more as functional description of the various features which may be present in a set of servers than as a structural schematic of the embodiments described herein. In practice, and as recognized by those of ordinary skill in the art, items shown separately could be combined and some items could be separated. For example, some items shown separately in FIG. 10 could be implemented on single servers and single items could be implemented by one or more servers. The actual number of servers used to implement a virtual surgery simulation system and how features are allocated among them will vary from one implementation to another, and may depend in part on the amount of data traffic that the system must handle during peak usage periods as well as during average usage periods.

According to various embodiments, the system includes software that implements a graphical user interface that allows students to take machine monitored tests and for teachers to use the results of the monitoring to analyze the student's performance. Similarly the system will incorporate software that presents the monitored factors and results in a format using graphical displays.

Figure 11:
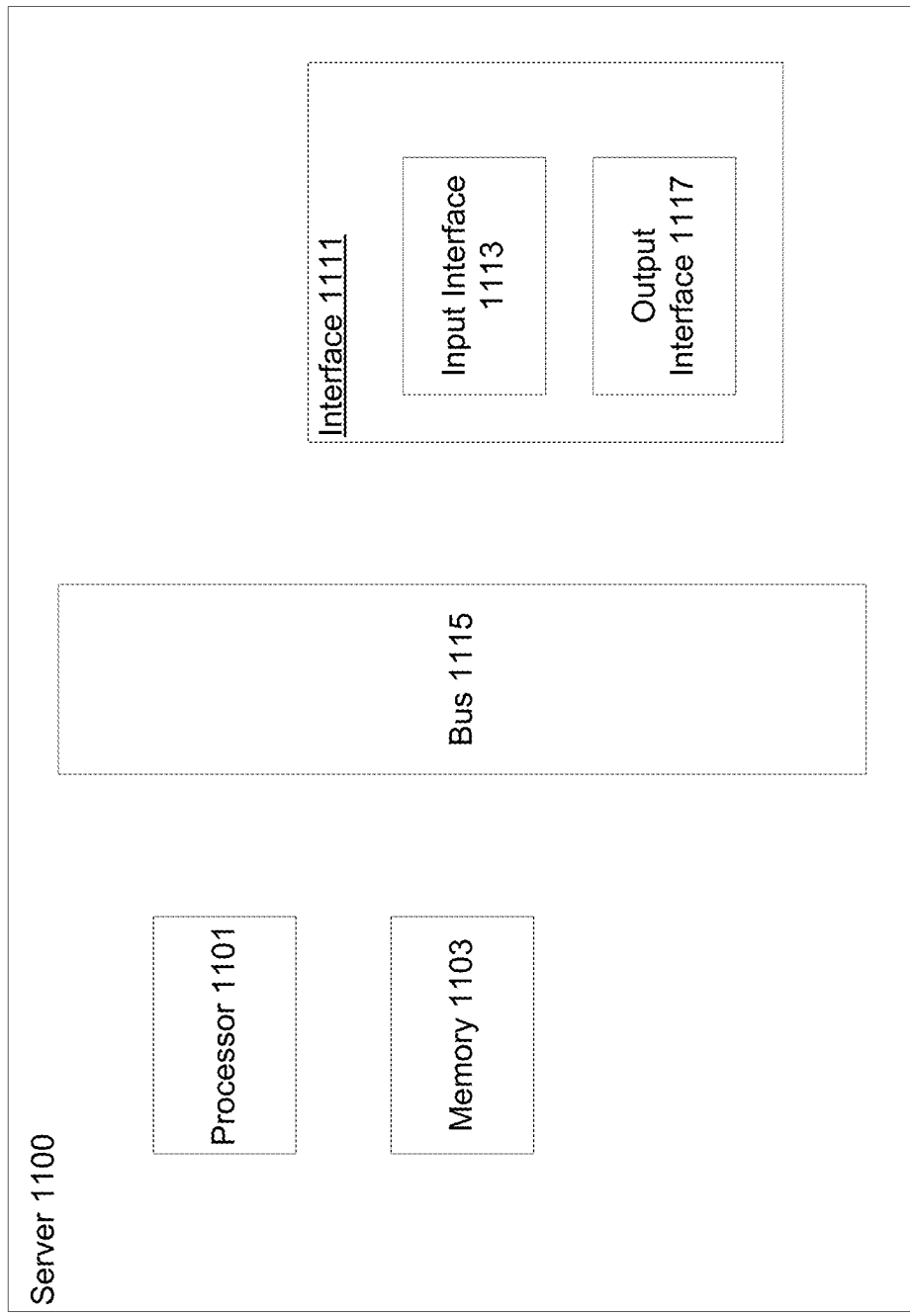
FIG. 11 shows one example of a server, in accordance with embodiments of the present disclosure.

FIG. 10, described above, illustrates a system architecture for educational analysis optimization. In some embodiments, the system architecture can be implemented using one or more servers. FIG. 11 illustrates an example of a server that can be used to implement the system architecture described in FIG. 10.

With reference to FIG. 11, shown is a particular example of a server that can be used to implement particular examples of the present disclosure. For instance, the server 1100 can be used to provide computation analysis according to various embodiments described above. According to particular example embodiments, a server 1100 suitable for implementing particular embodiments of the present disclosure includes a processor 1101, a memory 1103, an interface 1111, and a bus 1115 (e.g., a PCI bus). The interface 1111 may include separate input interface 1113 and output interface 1117, or may be a unified interface supporting both operations. When acting under the control of appropriate software or firmware, the processor 1101 is responsible for such tasks such as optimization. Various specially configured devices can also be used in place of a processor 1101 or in addition to processor 1101. The complete implementation can also be done in custom hardware. The interface 1111 is typically configured to send and receive data packets or data segments over a network. Particular examples of interfaces the device supports include Ethernet interfaces, frame relay interfaces, cable interfaces, DSL interfaces, token ring interfaces, and the like.

In addition, various very high-speed interfaces may be provided such as fast Ethernet interfaces, Gigabit Ethernet interfaces, ATM interfaces, HSSI interfaces, POS interfaces, FDDI interfaces and the like. Generally, these interfaces may include ports appropriate for communication with the appropriate media. In some cases, they may also include an independent processor and, in some instances, volatile RAM. The independent processors may control such communications intensive tasks as packet switching, media control and management.

According to particular example embodiments, the server 1100 uses memory 1103 to store data and program instructions and maintain a local side cache. The program instructions may control the operation of an operating system and/or one or more applications, for example. The memory or memories may also be configured to store received metadata and batch requested metadata.

Because such information and program instructions may be employed to implement the systems/methods described herein, the present disclosure relates to tangible, machine readable media that include program instructions, state information, etc. for performing various operations described herein. Examples of machine-readable media include hard disks, floppy disks, magnetic tape, optical media such as CD-ROM disks and DVDs; magneto-optical media such as optical disks, and hardware devices that are specially configured to store and perform program instructions, such as read-only memory devices (ROM) and programmable read-only memory devices (PROMs). Examples of program instructions include both machine code, such as produced by a compiler, and files containing higher level code that may be executed by the computer using an interpreter.

Although many of the components and processes are described above in the singular for convenience, it will be appreciated by one of skill in the art that multiple components and repeated processes can also be used to practice the techniques of the present disclosure.

While the present disclosure has been particularly shown and described with reference to specific embodiments thereof, it will be understood by those skilled in the art that changes in the form and details of the disclosed embodiments may be made without departing from the spirit or scope of the disclosure. It is therefore intended that the disclosure be interpreted to include all variations and equivalents that fall within the true spirit and scope of the present disclosure.

What is claimed is:

1. A system for educational analysis optimization, the system comprising:
   a camera;
   a processor; and
   memory, the memory storing instructions to cause a processor to execute a method, the method comprising:
      receiving a request from a user at a client device to begin a stimulus session;
      initializing video recording of the user for the stimulus session;
      calibrating recording cues for emotions and gaze;
      presenting one or more stimuli in the stimulus session;

recording cues and reactions during the stimulus session;

mapping the recorded cues and reactions to a content display timeline for the stimulus session;

post-processing the recorded cues and reactions for educational analysis; and providing feedback to the user.

2. The system of claim 1, wherein the stimulus session is a test taking session.

3. The system of claim 1, wherein the cues and reactions include one or more of the following: pulse, eye blink rate, eye movement, and pupil dilation.

4. The system of claim 1, wherein the stimulus session includes test questions, each test question being tagged with a difficulty level.

5. The system of claim 1, wherein post-processing the recorded cues and reactions includes calculating pacing throughout the stimulus session.

6. The system of claim 1, wherein providing feedback includes presenting a graphical representation of the user's performance during the stimulus session.

7. The system of claim 1, wherein the method further comprises optimizing the feedback provided using a predictive artificial intelligence model.

8. A method for educational analysis optimization, the method comprising:

receiving a request from a user at a client device to begin a stimulus session;

initializing video recording of the user for the stimulus session;

calibrating recording cues for emotions and gaze;

presenting one or more stimuli in the stimulus session;

recording cues and reactions during the stimulus session;

mapping the recorded cues and reactions to a content display timeline for the stimulus session;

post-processing the recorded cues and reactions for educational analysis; and providing feedback to the user.

9. The method of claim 8, wherein the stimulus session is a test taking session.

10. The method of claim 8, wherein the cues and reactions include one or more of the following: pulse, eye blink rate, eye movement, and pupil dilation.

11. The method of claim 8, wherein the stimulus session includes test questions, each test question being tagged with a difficulty level.

12. The method of claim 8, wherein post-processing the recorded cues and reactions includes calculating pacing throughout the stimulus session.

13. The method of claim 8, wherein providing feedback includes presenting a graphical representation of the user's performance during the stimulus session.

14. The method of claim 8, further comprising optimizing the feedback provided using a predictive artificial intelligence model.

15. A non-transitory computer readable medium storing instructions to cause a processor to execute a method, the method comprising:

receiving a request from a user at a client device to begin a stimulus session;

initializing video recording of the user for the stimulus session;

calibrating recording cues for emotions and gaze;

presenting one or more stimuli in the stimulus session;

recording cues and reactions during the stimulus session;

mapping the recorded cues and reactions to a content display timeline for the stimulus session;

post-processing the recorded cues and reactions for educational analysis; and providing feedback to the user.

16. The non-transitory computer readable medium of claim 15, wherein the stimulus session is a test taking session.

17. The non-transitory computer readable medium of claim 15, wherein the cues and reactions include one or more of the following: pulse, eye blink rate, eye movement, and pupil dilation.

18. The non-transitory computer readable medium of claim 15, wherein the stimulus session includes test questions, each test question being tagged with a difficulty level.

19. The non-transitory computer readable medium of claim 15, wherein post-processing the recorded cues and reactions includes calculating pacing throughout the stimulus session.

20. The non-transitory computer readable medium of claim 15, wherein providing feedback includes presenting a graphical representation of the user's performance during the stimulus session.

* * * * *